(12) United States Patent
Wang

(10) Patent No.: US 12,283,380 B2
(45) Date of Patent: Apr. 22, 2025

(54) SOMATOTYPE IDENTIFICATION METHOD, ACQUISITION METHOD OF HEALTH ASSESSMENT, APPARATUS AND DEVICE

(71) Applicant: BOE TECHNOLOGY GROUP CO., LTD., Beijing (CN)

(72) Inventor: Sifan Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 570 days.

(21) Appl. No.: 17/636,356

(22) PCT Filed: Apr. 30, 2021

(86) PCT No.: PCT/CN2021/091624
§ 371 (c)(1),
(2) Date: Feb. 17, 2022

(87) PCT Pub. No.: WO2022/227042
PCT Pub. Date: Nov. 3, 2022

(65) Prior Publication Data
US 2023/0352178 A1    Nov. 2, 2023

(51) Int. Cl.
*G16H 50/30* (2018.01)
*A61B 5/107* (2006.01)
*G06V 40/10* (2022.01)
*G16H 50/20* (2018.01)

(52) U.S. Cl.
CPC .............. *G16H 50/30* (2018.01); *A61B 5/107* (2013.01); *G06V 40/103* (2022.01); *G16H 50/20* (2018.01)

(58) Field of Classification Search
CPC ...... G16H 50/30; G16H 50/20; G06V 40/103; A61B 5/107
See application file for complete search history.

(56) References Cited

U.S. PATENT DOCUMENTS

| | | | |
|---|---|---|---|
| 2016/0279476 A1* | 9/2016 | Kim | G16H 20/30 |
| 2021/0001796 A1* | 1/2021 | Kudo | A61B 5/18 |
| 2021/0386409 A1* | 12/2021 | Clouse | A61B 5/742 |
| 2022/0087533 A1* | 3/2022 | El-Sallam | A61B 5/1079 |

FOREIGN PATENT DOCUMENTS

| | | |
|---|---|---|
| CN | 106666902 A | 5/2017 |
| CN | 108520221 A | 9/2018 |
| CN | 109409228 A | 3/2019 |
| CN | 110197165 A | 9/2019 |

\* cited by examiner

*Primary Examiner* — Syed Haider
(74) *Attorney, Agent, or Firm* — Intellectual Valley Law, P.C.

(57) ABSTRACT

A somatotype identification method, an acquisition method of health assessment, an apparatus, and a device provided by the present disclosure relates to the technical field of computer. The somatotype identification method includes: acquiring a body image of a user; performing a feature extraction on the body image, to obtain a predicted somatotype feature of the user; and screening a target somatotype category of the user from various somatotype categories according to the predicted somatotype feature.

16 Claims, 9 Drawing Sheets

Original image                Image data after the perspective transformation

SOMATOTYPE IDENTIFICATION METHOD, ACQUISITION METHOD OF HEALTH ASSESSMENT, APPARATUS AND DEVICE

TECHNICAL FIELD

The present disclosure relates to the technical field of computer, and in particular relates to a somatotype identification method, an acquisition method of health assessment, an apparatus, and a device.

BACKGROUND

Everyone has a unique genetic composition and a unique physiological structure, which determine that people have different somatotype categories. People with different somatotype categories have different requirements for dressing, exercise mode selection, body diagnosis, etc. Identifying the user's somatotype category enables better personalized recommendations for the users.

SUMMARY

The present disclosure provides a somatotype identification method, an acquisition method of health assessment, an apparatus, and a device.

Some embodiments of the present disclosure provide a somatotype identification method, and the method comprises:

acquiring a body image of a user;

performing a feature extraction on the body image, to obtain a predicted somatotype feature of the user; and screening a target somatotype category of the user from various somatotype categories according to the predicted somatotype feature.

Optionally, screening the target somatotype category of the user from the various somatotype categories according to the predicted somatotype feature comprises:

performing a similarity comparison between a standard somatotype feature corresponding to each somatotype category and the predicted somatotype feature, to obtain a similarity corresponding to each somatotype category;

calculating the similarity corresponding to each somatotype category by a classifier, to obtain a probability value of the user being each somatotype category; and regarding a somatotype category corresponding to a probability value that satisfies a probability value screening rule as the target somatotype category of the user.

Optionally, regarding the somatotype category corresponding to the probability value that satisfies the probability value screening rule as the target somatotype category of the user comprises:

acquiring a sort of probability values of various somatotype categories; and according to a somatotype category of which the sort of probability values is a target probability value sort, acquiring the target somatotype category of the user.

Optionally, at least two target probability value sorts exist;

the according to the somatotype category of which the sort of probability values is the target probability value sort, acquiring the target somatotype category of the user, comprises:

acquiring at least two target probability values which are probability values being the target probability value sorts, from the probability values corresponding to the various somatotype categories;

on the condition that a difference value between the at least two target probability values is greater than a probability threshold, regarding a somatotype category corresponding to the target probability value with a maximum value as the target somatotype category of the user; and on the condition that the difference value between the at least two target probability values is less than or equal to the probability threshold, regarding somatotype categories corresponding to the at least two target probability values, respectively, as the target somatotype categories of the user.

Optionally, the target probability value sorts comprise: a probability value sort being the first and a probability value sort being the second;

the acquiring at least two target probability values which are probability values being the target probability value sorts, from the probability values corresponding to the various somatotype categories, comprises:

acquiring a first probability value with the sort of probability values being the first and a second probability value with the sort of probability values being the second, from the probability values corresponding to the various somatotype categories, wherein the sort of probability values is sorted in descending order.

Optionally, calculating the similarity corresponding to each somatotype category by the classifier, to obtain the probability value of the user being each somatotype category, comprises:

inputting the similarity corresponding to each somatotype category into the following classifier formula, to obtain the probability value of the user being each somatotype category:

$$\text{soft target} = \frac{\exp(c(f(\hat{x}), f(x_i))/T)}{\sum_m \exp(c(f(\hat{x}), f(x_m))/T)}$$

wherein, the soft target is the probability value of a type category, $f(\hat{x})$ is the predicted somatotype feature, $f(x_i)$ is the standard somatotype feature for an $i^{th}$ somatotype category, $f(x_m)$ is the standard somatotype feature for a $m^{th}$ somatotype category, T is a constant parameter, $c(f(\hat{x}), f(x_i))$ is the similarity between the predicted somatotype feature and the $i^{th}$ standard somatotype feature, $c(f(\hat{x}), f(x_m))$ is the similarity between the predicted somatotype feature and the $m^{th}$ standard somatotype feature, $0<m\leq k$, $0<i\leq k$, k is a quantity of the somatotype categories, and i, m, k are positive integer, and the similarity includes at least one of the followings: a cosine similarity, a sine similarity, a Pearson coefficient, and a Jaccard coefficient.

Optionally, performing the feature extraction on the body image, to obtain a predicted somatotype feature of the user, comprises:

inputting the body image into a somatotype feature extraction model, to obtain the predicted somatotype feature of the user, wherein the somatotype feature extraction model is obtained by the following steps:

acquiring a sample body image labeled with the somatotype category;

performing a perspective transformation on the sample body image, to obtain a body image set; and training a somatotype feature extraction model to be trained according to the body image set, to obtain the somatotype feature extraction model for extracting the predicted somatotype feature.

Optionally, performing a perspective transformation on the sample body image, to obtain a body image set, comprises:

based on vertexes of a target frame region in the sample body image, performing the perspective transformation according to a target zoom range, and combining a plurality of obtained body images into the body image set, wherein the target frame region is an image region where a body of the user is located.

Optionally, before the step of based on the vertexes of the target frame region in the sample body image, performing the perspective transformation according to the target zoom range, and combining the plurality of obtained body images into the body image set, the method further comprises:

scaling an original size of the sample body image according to a preset ratio, to obtain the target zoom range.

Optionally, training the somatotype feature extraction model to be trained according to the body image set, to obtain the somatotype feature extraction model for extracting the predicted somatotype feature, comprises:

dividing the body image set into a training set and a test set;

inputting the training set into the somatotype feature extraction model to be trained for training, to obtain a trained somatotype feature extraction model;

inputting a first sample body image corresponding to various somatotype categories of the training set and a second sample body image corresponding to any somatotype category of the test set into the trained somatotype feature extraction model, to obtain a first sample predicted feature of each first sample body image and a second sample predicted feature of the second sample body image; and in the case of determining that the first sample predicted feature and the second sample predicted feature satisfy a training requirement, ending the training.

Optionally, determining that the first sample predicted features and the second sample predicted feature satisfy the training requirement comprises:

acquiring a sample similarity between the first sample predicted feature and the second sample predicted feature;

inputting the sample similarity into a loss function, to obtain a loss value; and on the condition that the loss value satisfies a model training requirement, determining that the first sample predicted feature and the second sample predicted feature satisfy the training requirement.

Some embodiments of the present disclosure provide an acquisition method of health assessment, and the method comprises:

acquiring the target somatotype category of the user by the somatotype identification method according to any one of the above embodiments;

acquiring health assessment information according to the target somatotype category; and providing the health assessment information for the user.

Optionally, the acquiring health assessment information according to the target somatotype category comprises:

adjusting the target somatotype category according to a target category dimension, to obtain an actual somatotype category of the user; and querying the health assessment information matching the actual somatotype category from a health assessment information base.

Optionally, querying the health assessment information matching the actual somatotype category from a health assessment information base comprises:

querying disease prediction information matching the actual somatotype category from the health assessment information base as the health assessment information of the user.

Some embodiments of the present disclosure provide a somatotype identification apparatus, and the apparatus comprises:

an acquisition module configured to acquire a body image of a user;

an identification module configured to perform a feature extraction on the body image, to obtain a predicted somatotype feature of the user; and screen a target somatotype category of the user from various somatotype categories according to the predicted somatotype feature.

Optionally, the identification module is further configured to:

perform a similarity comparison between a standard somatotype feature corresponding to each somatotype category and the predicted somatotype feature, to obtain a similarity corresponding to each somatotype category;

calculate the similarity corresponding to each somatotype category by a classifier, to obtain a probability value of the user being each somatotype category; and regard a somatotype category corresponding to a probability value that satisfies a probability value screening rule as the target somatotype category of the user.

Optionally, the identification module is further configured to:

acquire a sort of probability values of various somatotype categories; and according to a somatotype category of which the sort of probability values is a target probability value sort, acquire the target somatotype category of the user.

Optionally, at least two target probability value sorts exist;

the identification module is further configured to:

acquire at least two target probability values which are probability values being the target probability value sorts, from the probability values corresponding to the various somatotype categories;

on the condition that a difference value between the at least two target probability values is greater than a probability threshold, regard a somatotype category corresponding to the target probability value with a maximum value as the target somatotype category of the user; and on the condition that the difference value between the at least two target probability values is less than or equal to the probability threshold, regard somatotype categories corresponding to the at least two target probability values, respectively, as the target somatotype categories of the user.

Optionally, the target probability value sorts comprise: a probability value sort being the first and a probability value sort being the second;

the identification module is further configured to:

acquire a first probability value with the sort of probability values being the first and a second probability value with the sort of probability values being the second, from the probability values corresponding to the various somatotype categories, wherein the sort of probability values is sorted in descending order.

Optionally, the identification module is further configured to:

input the similarity corresponding to each somatotype category into the following classifier formula, to obtain the probability value of the user being each somatotype category:

$$\text{soft target} = \frac{\exp(c(f(\hat{x}), f(x_i))/T)}{\sum_m \exp(c(f(\hat{x}), f(x_m))/T)}$$

wherein, the soft target is the probability value of a type category, $f(\hat{x})$ is the predicted somatotype feature, $f(x_i)$ is the standard somatotype feature for an $i^{th}$ somatotype category, $f(x_m)$ is the standard somatotype feature for a $m^{th}$ somatotype category, T is a constant parameter, $c(f(\hat{x}), f(x_i))$ is the similarity between the predicted somatotype feature and the $i^{th}$ standard somatotype feature, $c(f(\hat{x}), f(x_m))$ is the similarity between the predicted somatotype feature and the $m^{th}$ standard somatotype feature, $0<m\leq k$, $0<i\leq k$, k is a quantity of the somatotype categories, and i, m, k are positive integer, and the similarity comprises at least one of the followings: a cosine similarity, a sine similarity, a Pearson coefficient, and a Jaccard coefficient.

Optionally, the identification module is further configured to:

input the body image into a somatotype feature extraction model, to obtain the predicted somatotype feature of the user, wherein the somatotype feature extraction model is obtained by the following steps:

acquire a sample body image labeled with the somatotype category;

perform a perspective transformation on the sample body image, to obtain a body image set; and train a somatotype feature extraction model to be trained according to the body image set, to obtain the somatotype feature extraction model for extracting the predicted somatotype feature.

Optionally, the identification module is further configured to:

based on vertexes of a target frame region in the sample body image, perform the perspective transformation according to a target zoom range, and combine a plurality of obtained body images into the body image set, wherein the target frame region is an image region where a body of the user is located.

Optionally, the identification module is further configured to:

scale an original size of the sample body image according to a preset ratio, to obtain the target zoom range.

Optionally, the identification module is further configured to:

divide the body image set into a training set and a test set;

input the training set into the somatotype feature extraction model to be trained for training, to obtain a trained somatotype feature extraction model;

input a first sample body image corresponding to each somatotype category of the training set and a second sample body image corresponding to any somatotype category of the test set into the trained somatotype feature extraction model, to obtain a first sample predicted feature of each first sample body image and a second sample predicted feature of the second sample body image; and in the case of determining that the first sample predicted feature and the second sample predicted feature satisfy a training requirement, end the training.

Optionally, the identification module is further configured to:

acquire a similarity between the first sample predicted feature and the second sample predicted feature;

input the similarity into a loss function, to obtain a loss value;

on the condition that the loss value satisfies a model training requirement, determine that the first sample predicted feature and the second sample predicted feature satisfy the training requirement.

Some embodiments of the present disclosure provide an acquisition apparatus of health assessment, and the apparatus comprises:

an input module configured to acquire the target somatotype category of the user by the somatotype identification method according to any one of the above embodiments;

a query module configured to acquire health assessment information according to the target somatotype category; and an output module configured to provide the health assessment information for the user.

Optionally, the query module is further configured to:

adjust the target somatotype category according to a target category dimension, to obtain an actual somatotype category of the user; and query the health assessment information matching the actual somatotype category from a health assessment information base.

Optionally, the query module is further configured to:

query disease prediction information matching the actual somatotype category from the health assessment information base as the health assessment information of the user.

Some embodiments of the present disclosure provide a computing and processing device, comprising:

a memory storing a computer-readable code; and one or more processors, wherein when the computer-readable code is executed by the one or more processors, the computing and processing device implements the somatotype identification method according to the above or the acquisition method of health assessment according to the above.

Some embodiments of the present disclosure provide a computer program, wherein the computer program comprises a computer-readable code, and when the computer-readable code is executed on a computing and processing device, the computer-readable code causes the computing and processing device to implement the somatotype identification method according to the above or the acquisition method of health assessment according to the above.

Some embodiments of the present disclosure provide a computer-readable medium, wherein the computer-readable medium stores the computer program of the somatotype identification method according to the above or the acquisition method of health assessment according to the above.

The above description is merely a summary of the technical solutions of the present disclosure. In order to more clearly know the elements of the present disclosure to enable the implementation according to the contents of the description, and in order to make the above and other purposes, features, and advantages of the present disclosure more apparent and understandable, the particular embodiments of the present disclosure are provided below.

BRIEF DESCRIPTION OF THE DRAWINGS

In order to more clearly illustrate the technical solutions of the embodiments of the present disclosure or the prior art, the figures that are required to describe the embodiments or the prior art will be briefly introduced below. Apparently, the figures that are described below are embodiments of the present disclosure, and a person skilled in the art can obtain other figures according to these figures without paying creative work. It should be noted that the ratios in the drawings are merely illustrative and do not represent actual ratios.

DETAILED DESCRIPTION OF THE EMBODIMENTS

In order to make the objects, the technical solutions, and the advantages of the embodiments of the present disclosure clearer, the embodiments of the present disclosure will be clearly and completely described below with reference to the drawings of the embodiments of the present disclosure. Apparently, the described embodiments are merely certain embodiments of the present disclosure, rather than all of the embodiments. All of the other embodiments that a person skilled in the art obtains on the basis of the embodiments of the present disclosure without paying creative work fall within the protection scope of the present disclosure.

In the related art, a full-body photo of a user is taken, and then according to the user's height information, etc., the image recognition technology is used to identify the human body contour, and according to preset line segments the size data of the body parts such as bust, waist, and hip circumference are calculated. Finally, the size data of each body part are compared with the standard template data to obtain the user's somatotype category.

Figure 1:
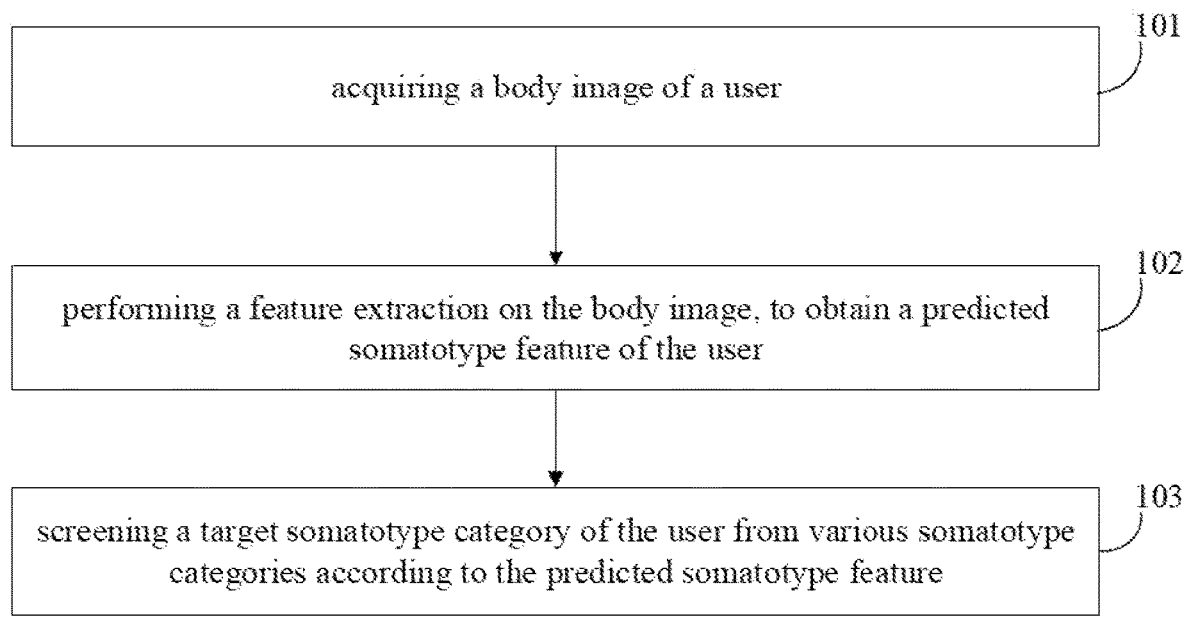
FIG. 1 schematically illustrates a first flow chart of a somatotype identification method according to some embodiments of the present disclosure.

FIG. 1 schematically illustrates a flow chart of a somatotype identification method according to some embodiments of the present disclosure. A executive subject of the method may be any electronic device, for example, it may be applied to an application program with a somatotype identification function, and the method may be executed by a server or a terminal device of the application program. Optionally, the method may be executed by the server, and the method includes:

step 101, acquiring a body image of a user.

In the embodiment of the present disclosure, the user refers to a person who needs to be identified the somatotype through the method according to the embodiment of the present disclosure. The user may be any user, for example, may be any registered user of the above application program. The body image refers to an image obtained by photographing the user's body through an electronic device with an image acquisition function, such as a camera, a video camera, and a mobile phone. Wherein, the body image may include the complete body of the user as much as possible to improve the accuracy of subsequent identification. The user may not wear clothes or wear clothes, and the body image may be a front body photo of the user, a back body photo of the user, and a side body photo that can reflect the complete body outline of the user. It is worth noting that the clothing worn by the user may be clothing that does not block the body outline as much as possible, such as intimate clothing, tight clothing, swimwear, etc., which can be determined according to actual needs, and it is not limited here.

In practical applications, the body image may be obtained by cooperating with two users, who are the photographer and the subject, respectively. The image acquisition device is placed as perpendicular to the ground as possible, and the subject keeps his limbs stretched as much as possible without blocking the body outline, so that the photographer may shoot the front or back of the subject by controlling the image acquisition device to obtain the body image of the subject.

Step 102, performing a feature extraction on the body image, to obtain a predicted somatotype feature of the user.

In some embodiments of the present disclosure, the somatotype feature extraction model has an image feature identification function which is used to extract features in the body image. In some embodiments, the somatotype feature extraction model may be obtained by a deep learning model. For example, the deep learning model may use a visual geometry group network (VGG) model, a residual network model, etc., and all deep learning networks with image feature extraction functions are applicable to the embodiments of the present disclosure.

For example, in a scenario where there are few samples of the body images that can be obtained, the somatotype feature extraction model may be a small sample learning model that may identify the user's body outline in the body image. In some embodiments, the deep learning model may be a one-shot learning model or a few-shot learning model. One-shot learning model or few-shot learning model may be used for training with a small quantity of samples.

Whether to learn through small samples depends on the quantity of training samples, which can be set according to actual needs, and it is not limited here.

The predicted somatotype feature refers to a prediction result of the somatotype feature extraction model for the body image. The predicted somatotype feature is a feature extracted by a convolutional network in the somatotype feature extraction model. Different predicted somatotype features will be obtained by different body images processed through the convolutional network. The predicted somatotype feature may be in the form of a feature vector, and the feature vector may be an array from 1-dimension to N-dimension, or a feature map with high-dimension, wherein each dimension may include abstract dimensions such as texture, color, position, and so on.

In some embodiments provided in the present disclosure, the somatotype feature extraction model may further include a convolutional network, and multiple convolutional layers may be set in the convolutional network according to actual requirements, specifically according to the performance requirements for the somatotype feature extraction model to set the hierarchical structure of the somatotype feature extraction model. Further, the predicted somatotype feature may also be obtained by using a splitter to perform a color segmentation on the colors contained by the user's body in the body image. As long as the specific feature extraction method can output the predicted somatotype feature required by the present disclosure, and it is not limited here.

In practical applications, the somatotype feature extraction model may be obtained by pre-training, or the somatotype feature extraction model may be trained first and then used. The trained somatotype feature extraction model may identify the predicted somatotype feature in the body image, so that the somatotype feature extraction model can output the predicted somatotype feature which can reflect of the user's somatotype category.

Step 103, screening a target somatotype category of the user from various somatotype categories according to the predicted somatotype feature.

Figure 2:
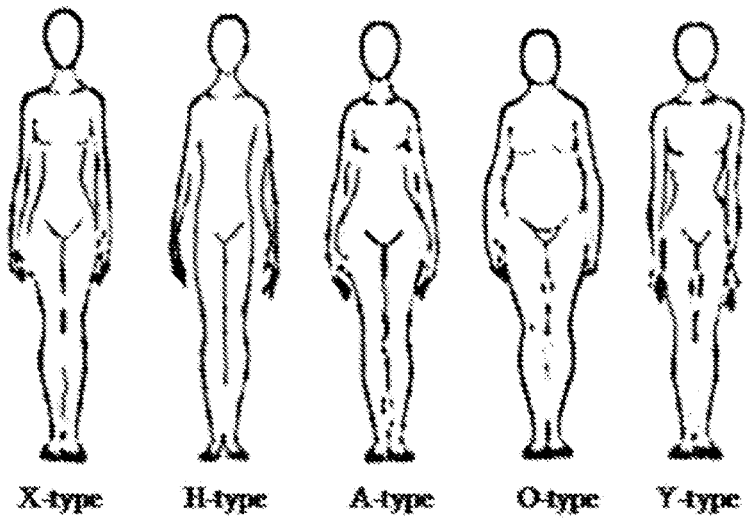
FIG. 2 schematically illustrates a schematic diagram of a somatotype identification method according to some embodiments of the present disclosure.

In the embodiment of the present disclosure, the somatotype category refers to the classification of the body type of the human body. For example, referring to FIG. 2, the somatotype category of the user may be divided into a A-type (pear type), a H-type (banana type), a X-type (hourglass type), a O-type (apple type), a Y-type (funnel type) and other somatotype categories, according to the outline of the body type. Certainly, it may be further divided according to other division rules, which are related to the image features that can be reflected in the body image, and it is enough to ensure that the somatotype feature extraction model can identify. Specifically, different somatotype categories can be divided according to actual needs, which can be set according to actual needs, and which is not limited here. The quantity of the somatotype categories can be set according to actual needs, and it is not limited here.

In some embodiments, by analyzing the predicted somatotype feature, various somatotype categories are screened according to a screening rule, and a desired somatotype category is screened out as the target somatotype category of the user. The screening rule may regard the somatotype category with a largest probability value as the target somatotype category, or the somatotype category with a probability value centered in the probability values as the target somatotype category. Certainly, the predicted somatotype category may be further processed to obtain a more accurately determination reference data to screen the somatotype category, the specific can be determined according to the actual needs, and which is not limited here.

In the embodiment of the present disclosure, the target somatotype category of the user may be screened from various somatotype categories according to the predicted image features extracted from the body image of the user, and the somatotype category of the user may be accurately identified without relying on a somatotype template, thereby improving the accuracy of the somatotype identification.

Figure 3:
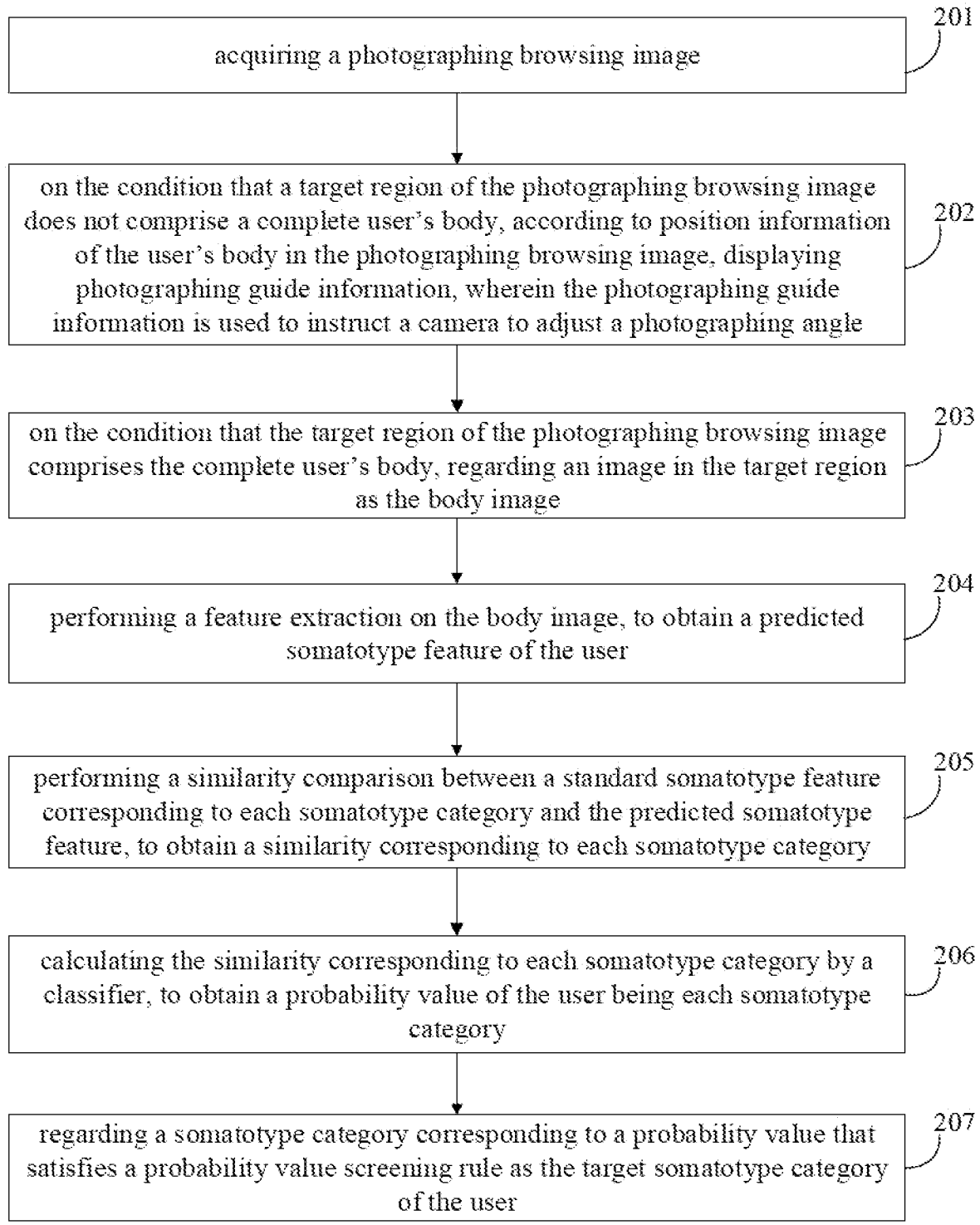
FIG. 3 schematically illustrates a second flow chart of a somatotype identification method according to some embodiments of the present disclosure.

FIG. 3 schematically illustrates a flow chart of a somatotype identification method according to some embodiments of the present disclosure, and the method includes:

step 201, acquiring a photographing browsing image.

In the embodiment of the present disclosure, the photographing browsing image refers to an image collected by a camera of the image acquisition device, and the image may be displayed to the user through the screen, so that the user may adjust a photographing angle of the camera with reference to the effect of the photographing browsing image.

Step 202, on the condition that a target region of the photographing browsing image does not include a complete user's body, according to position information of the user's body in the photographing browsing image, displaying photographing guide information, wherein the photographing guide information is used to instruct a camera to adjust a photographing angle.

In the embodiment of the present disclosure, the target region refers to an image display region where the user's body needs to be located in the photographing browsing image. The target region may be determined by the image acquisition device by automatically detecting the user's body, or may be set by the user. The purpose of the target display region is to provide a reference for subsequent acquisition of the body images. For example, according to the built-in gyroscope signal of the photographing device such as mobile phones, tablet computers, cameras, etc., the photographer is instructed to place the photographing device vertically. After the body of the photographing device is vertical, a reference frame is displayed in the photographing browsing image on the screen, the photographer moves the body of the photographing device to make the whole subject's body enters the reference frame to shoot.

Specifically, if the complete user's body does not exist in the target region, that is, if the user's body does not exist in the target region, or only a part of the user's body exists, then the image acquisition device may, according to the position of the user's body in the target region, displaying photographing information on the screen for guiding the user to adjust the photographing angle of the camera. For example: if there is no users body in the target region, the photographing guide information may be "Please aim the camera at the person"; if the target region only has the users upper body below, the photographing guide information may be "Please move the camera up"; if the target region only includes part of the user's body, but the entire target region is the user's body, it means that the camera is too close to the user, and the photographing guide information may be "please move the camera back" and so on. Certainly, this is only an exemplary description, the specific setting method of the photographing guide information may be set according to actual needs, and which is not limited here.

Step 203, on the condition that the target region of the photographing browsing image includes the complete user's body, regarding an image in the target region as the body image.

In the embodiment of the present disclosure, the user's body in the photographing browsing image may be detected by an image identification technology, and whether there is a complete user's body in the target region is determined according to the quantity of the identified user's body parts. The image identification technology in the related art may be referenced, and it will not be repeated here. When it is determined that the target region contains a complete user's body, the image in the target region may be extracted as a body image required for somatotype identification.

Step 204, performing a feature extraction on the body image, to obtain a predicted somatotype feature of the user.

For this step, reference may be made to the detailed description of step 102, which will not be repeated here.

Step 205, performing a similarity comparison between a standard somatotype feature corresponding to each somatotype category and the predicted somatotype feature, to obtain a similarity corresponding to each somatotype category.

In the embodiment of the present disclosure, the standard somatotype feature is a standard feature corresponding to each somatotype category used as a reference. Specifically, it may be obtained by processing the body image of each somatotype category with high quality by the somatotype feature extraction model. The standard somatotype feature may be prepared in advance, or it may be obtained during the identification process of the body image. In order to improve the efficiency of somatotype identification, the standard somatotype feature may be prepared in advance, and there is no need to repeat the extraction during the identification process.

Step 206, calculating the similarity corresponding to each somatotype category by a classifier, to obtain a probability value of the user being each somatotype category.

In some embodiments, the obtained value of similarity corresponding to each somatotype category is input into the classifier, to calculate the probability value of the user being each somatotype category.

In some embodiments of the present disclosure, the predicted somatotype feature and the standard somatotype feature are calculated by the following formula (1) to obtain the classification probability of the user being each somatotype category:

$$\text{soft target} = \frac{\exp(c(f(\hat{x}), f(x_i))/T)}{\sum_m \exp(c(f(\hat{x}), f(x_m))/T)} \quad (1)$$

Wherein, the soft target is the probability value of a type category, $f(\hat{x})$ is the predicted somatotype feature, $f(x_i)$ is the standard somatotype feature for an $i^{th}$ somatotype category, $f(x_m)$ is the standard somatotype feature for a $m^{th}$ somatotype category, T is a constant parameter, $c(f(\hat{x}), f(x_i))$ is the similarity between the predicted somatotype feature and the $i^{th}$ standard somatotype feature, $c(f(\hat{x}), f(x_m))$ is the similarity between the predicted somatotype feature and the $m^{th}$ standard somatotype feature, $0<m\leq k$, $0<i\leq k$, k is a quantity of the somatotype categories, and i, m, k are positive integer, and the similarity includes at least one of the followings: a cosine similarity, a sine similarity, a Pearson coefficient, and a Jaccard coefficient.

In some embodiments, for example, the value of T is 20. The value of T may be adjusted according to the experimental effect, and which is not limited here.

It is worth noting that the softmax in the following formula 2 may also be used as the classifier network to calculate the classification probability of the user being each somatotype category:

$$\text{softmax} = \frac{\exp(z_i)}{\sum_j \exp(z_i)} \quad (2)$$

Wherein, $Z_i$ is a similarity of the $i^{th}$ somatotype category, j is the quantity of the somatotype categories.

When using the softmax as the classifier, a neural network extracts the output parameters of the last layer of the feature, such as 5, 2, −1, 3, which are calculated by the softmax to obtain 0.842, 0.042, 0.002, and 0.114. In the case of using the soft target, if T=10 in the soft target is set, 0.32, 0.23, 0.17, and 0.26 are calculated, and the data distribution of probability prediction is obviously more moderate than that of the softmax. The reason is that in extreme cases, our training data has only one body image in a somatotype category. Although the data is expanded through data enhancement and other methods, it is still essentially the somatotype category of the same person, and it is impossible to learn the somatotype features of multiple people of the same somatotype. There will be some "bias" errors when the model searches similar somatotypes; in addition, the classification of somatotype categories often appears mixtures, such as the A somatotype category behaves like the O somatotype category when obese, and the model may only retain the most significant features of the O somatotype category, and ignore the somatotype feature of the A somatotype category, these all increase the difficulty of the model's identification. In the actual use process, the prediction probability data is moderated, which helps the model to be fault-tolerant and improves the accuracy of the model prediction. For example, when the similarity of the predicted somatotype feature of the sample body image is compared with the similarity of the standard somatotype feature, the model without the T parameter considers that the sample body image is the most similar to the A somatotype category, and the others are not considered, and the model with the T parameter added predicts more moderately, the difference between the first two probability values is less than the threshold, then it can be said that the somatotype category of the sample body image is the closest to the A somatotype category, and it is also a bit like the O somatotype category, there have the disease probability of both somatotype categories.

In some embodiments, the cosine value between the standard somatotype feature corresponding to each somatotype category and the predicted somatotype feature may be calculated, respectively, to obtain multiple similarities. Since the predicted somatotype feature of the user is extracted based on the user's somatotype image in the present disclosure, when the somatotype image is a two-dimensional image, the cosine similarity may better reflect the similarity between the two-dimensional images. Certainly, if the somatotype image is a three-dimensional image, or a one-bit data set obtained by converting the two-dimensional image, it may also use other similarities suitable for the body image dimension, which can be set according to actual needs, and which is not limited here.

Step 207, regarding a somatotype category corresponding to a probability value that satisfies a probability value screening rule as the target somatotype category of the user.

In the embodiment of the present disclosure, the somatotype category of the user may be screened out from various somatotype categories according to the probability value screening rule referring to the above-mentioned classification probability.

In some embodiments, the data of the classification probability may be sorted in descending order, and then screen out the somatotype category sorted in the first, or the somatotype category sorted in the second or the third with the data of the classification probability sorted in descending order. Specifically, the probability value screening rule may be set according to actual needs, which is not limited here. For example, it can also be the somatotype category sorted in the last with the data of the classification probability sorted in ascending order, or the somatotype category sorted in the second-to-last in ascending order. Specifically, the probability value screening rule can be set according to actual needs, which is not limited here.

Figure 4:
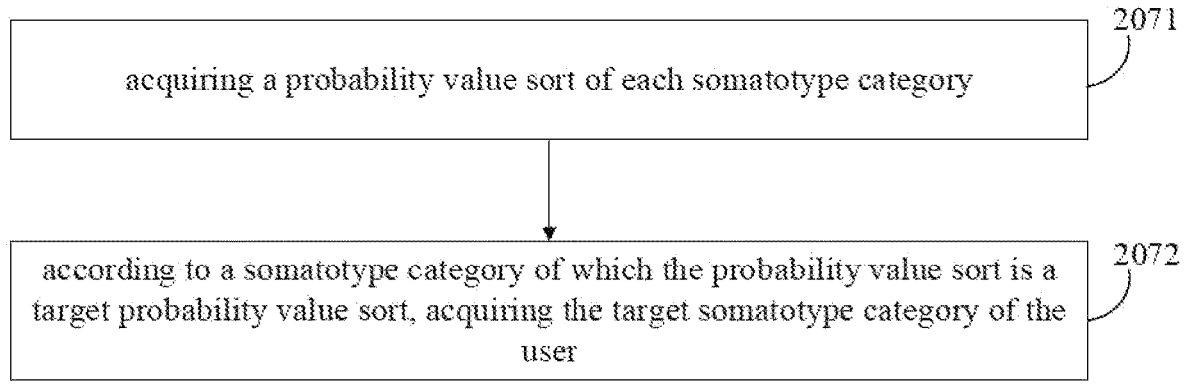
FIG. 4 schematically illustrates a third flow chart of a somatotype identification method according to some embodiments of the present disclosure.

Optionally, referring to FIG. 4, the step 207 includes:

sub-step 2071, acquiring a sort of probability values of various somatotype categories In some embodiments of the present disclosure, the sort of probability values may be sorted in ascending order or descending order according to the probability value of the somatotype category.

Sub-step 2072, according to a somatotype category of which the sort of probability values is a target probability value sort, acquiring the target somatotype category of the user.

In some embodiments of the present disclosure, the target probability value sort may be the first, the second, or the tailender and the penultimate in the sort of probability values, or it may be a specified probability value sort in the middle. The target probability value sort may be set by the user, or it may be automatically set based on the sorting method of the sort of probability values, the quantity of the somatotype categories participating in the sorting and other related parameters, which may be set according to actual needs, and it is not limited here.

In some embodiments of the present disclosure, the target somatotype category may be obtained by further screening the somatotype category being the target probability value sort, for example, the somatotype category of the target probability value sort sorted in the first two or the last two is used as the target somatotype category, or the somatotype category in which the target probability value sort is centered is used as the target somatotype category, and the obtained target somatotype category may also be one or at least two or more, which can be set according to actual needs, and it is not limited here.

Figure 5:
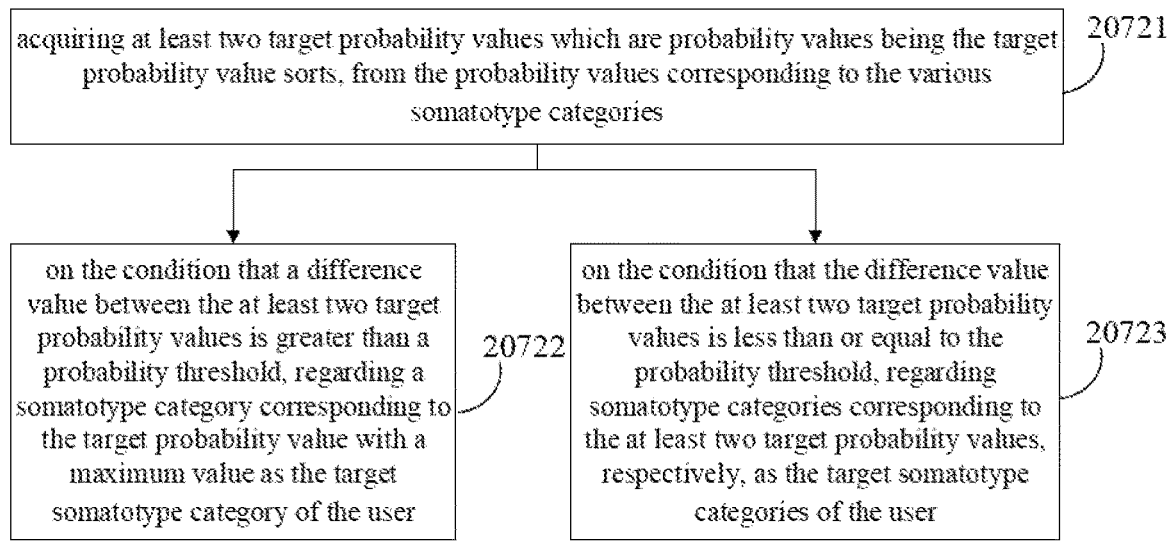
FIG. 5 schematically illustrates a fourth flow chart of a somatotype identification method according to some embodiments of the present disclosure.

Optionally, referring to FIG. 5, the sub-step 2072 includes:

sub-step 20721, acquiring at least two target probability values which are probability values being the target probability value sorts, from the probability values corresponding to the various somatotype categories.

In some embodiments provided by the present disclosure, the sort of probability values may be sorted in ascending order or may be sorted in descending order according to the probability values, and the target probability value sort is the specified sort in the sort of probability values, the target probability value sort may exist two or more to facilitate subsequent probability value analysis. For example: usually the somatotype category with the largest probability value may be used as the user's somatotype category, but considering that the somatotype category of some users is between the two somatotype categories, it is necessary to further screen the plurality of somatotype categories with the top probability values.

Sub-step 20722, on the condition that a difference value between the at least two target probability values is greater than a probability threshold, regarding a somatotype category corresponding to the target probability value with a maximum value as the target somatotype category of the user.

In some embodiments provided in the present disclosure, when the difference value between the at least two target probability values is greater than the probability threshold, it can indicate that the user's somatotype category is only a somatotype category corresponding to one target probability value with a high probability, and then the somatotype category corresponding to the target probability value with the maximum value is used as the user's somatotype category.

Sub-step 20723, on the condition that the difference value between the at least two target probability values is less than or equal to the probability threshold, regarding somatotype categories corresponding to the at least two target probability values, respectively, as the target somatotype categories of the user.

In the embodiment of the present disclosure, when the difference value between the at least two target probability values is less than or equal to the probability threshold, although there is a difference between the at least two target probability values, the user's somatotype with the high probability is between the somatotype categories corresponding to the at least two target probability values, so the somatotype categories corresponding to the at least two target probability values may be used as the somatotype categories of the user.

Optionally, the target probability value sorts include: a probability value sort being the first and a probability value sort being the second, the sub-step 20721 includes: acquiring a first probability value with the sort of probability values being the first and a second probability value with the sort of probability values being the second, from the probability values corresponding to the various somatotype categories, wherein the sort of probability values is sorted in descending order.

In some embodiments provided by the present disclosure, when the sort of probability values is sorted in ascending order, the tailender probability value sort is the first probability value, and the penultimate probability value sort is the second probability value. Usually, the somatotype category with the largest probability value may be used as the user's somatotype category, but considering that the somatotype category of some users is between the two somatotype categories, it is necessary to further screen out the first two probability values of the top probability values, that is, the first probability value and the second probability value are used for further determination. In the embodiment of the present disclosure, when the difference value between the first probability value and the second probability value is less than or equal to the probability threshold, the difference between the first probability value and the second probability value is small, the user's somatotype with the high probability is between the two somatotype categories, so the somatotype categories corresponding to the first probability value and the second probability value, respectively, may be used as the user's somatotype categories, and the probability threshold may be set according to actual needs. For example, if the difference between the first probability value and the second probability value exceeds 10%, the somatotype category corresponding to the first probability value is taken; if it is less than 10%, the somatotype categories corresponding to the first probability value and the second probability value are taken. For example, when the probabilities of the user being in the H-type and the Y-type somatotype category are 35% and 42%, respectively, and the difference between the probabilities of the two is less than 10%, both the H-type and the Y-type are used as the user's somatotype categories.

In the embodiment of the present disclosure, in the sort of probability values corresponding to various somatotype categories, when the difference between the probability values of the target probability value sort is small, it is determined that the user is a comprehensive somatotype category between at least two somatotype categories, which further ensures the accuracy of the somatotype identification.

Figure 6:
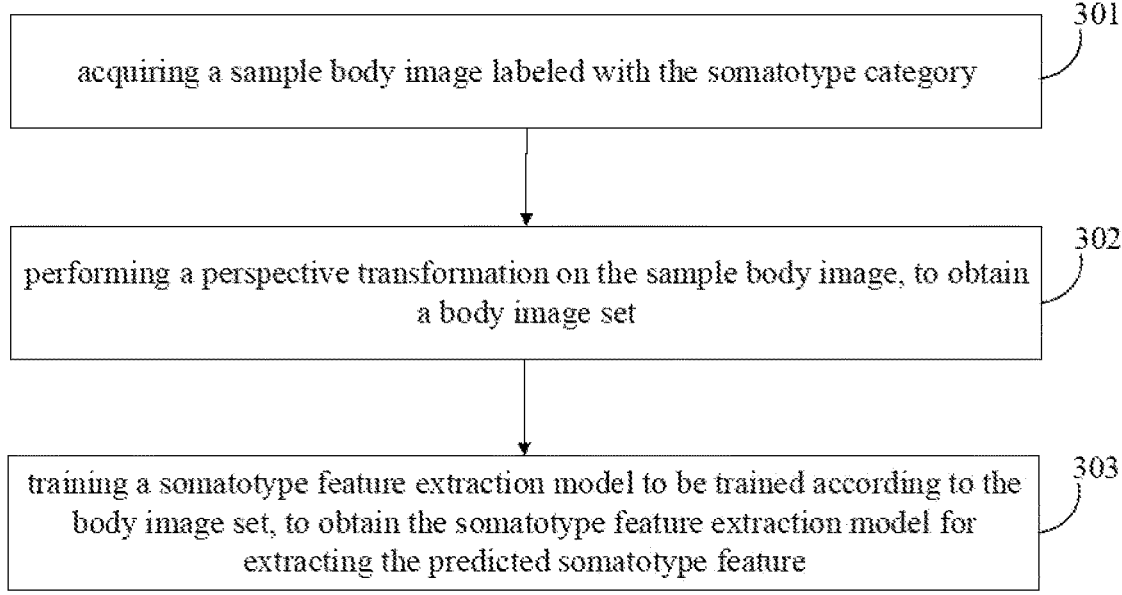
FIG. 6 schematically illustrates a first flow chart of a training method of a somatotype feature extraction model according to some embodiments of the present disclosure.

Optionally, FIG. 6 schematically illustrates a flow chart of a training method of a somatotype feature extraction model according to some embodiments of the present disclosure, and the method includes:

step 301, acquiring a sample body image labeled with the somatotype category.

In the embodiment of the present disclosure, the sample body image is similar to the user's body image in step 101, except that the sample body image is labeled with the somatotype category, that is, a label reflecting the somatotype category is pre-added to the sample body image, so that the somatotype feature extraction model to be trained may learn the somatotype category in the sample body image by model training.

In practical applications, after the sample body image is acquired, the user's somatotype category is labeled in the sample body image by manually or a sample labeling model to complete the labeling process for the training samples. The sample standard model may refer to related art, which needs to complete the labeling process for the sample body image.

Step 302, performing a perspective transformation on the sample body image, to obtain a body image set.

In the embodiment of the present disclosure, the perspective transformation is an image transformation technology by using the condition that the perspective center, the image point, and the target point are collinear, and according to the law of perspective rotation, to make the shadow-bearing surface, the perspective surface, the winding traces, and the perspective axis rotate at a certain angle, which transforms the original projected light beam and can still maintain the projected geometry on the shadow-bearing surface unchanged. By processing the sample body image through perspective transformation, a body image set that reflects the sample body images of the user at different angles may be obtained. It is worth noting that the sample body image taken by the user at a single photographing angle may only reflect the image feature of the user at the photographing angle, and cannot fully reflect the image features of the user at different photographing angles. The body image set obtained by the perspective transformation is obtained by performing perspective transformation based on the sample body image. On the basis that each sample body image contains the user's body, due to the change of the projected light beam, causing that each sample body image presents different photographing angles. So the body image set can reflect the image features of the user's body under multiple different photographing angles.

In practical applications, the perspective transformation may be performed by using the function cv2.getPerspectiveTransform( ) provided in OpenCV (a cross-platform computer vision and machine learning software library), the perspective transformation of the sample body image may be realized by selecting a specified number of coordinates such as 2, 4, and 6 in the sample body image as the transformation vertex coordinate. It is worth noting that the quantity of images in the body image set obtained by perspective transformation may be set as many as possible on the condition that the computing resources are allowed, so that the body image set may reflect different photographing angles as much as possible, to ensure the adequacy of the body image set. Certainly, the sample body image may also be processed by data enhancement methods such as horizontal flipping, contrast adjustment, and color adjustment in the related art, to improve the quality of the training samples.

Figure 7:
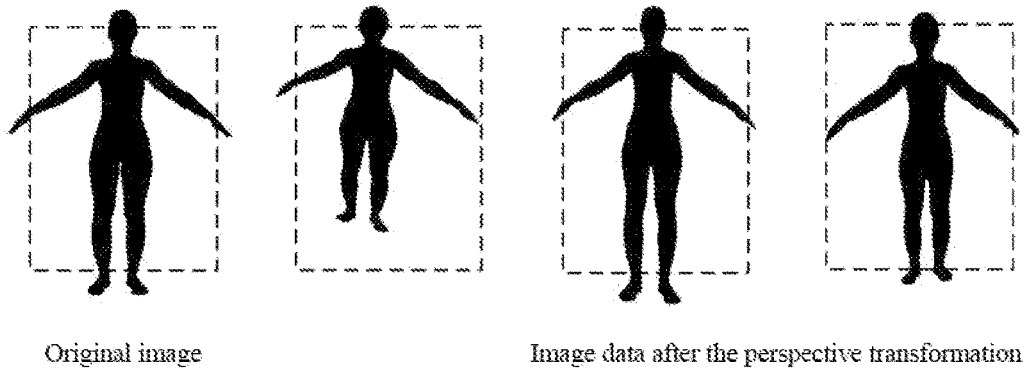
FIG. 7 schematically illustrates a first schematic diagram of a training method of a somatotype feature extraction model according to some embodiments of the present disclosure.

Exemplarily, referring to FIG. 7, after performing perspective transformation on one sample body image that can only reflect one photographing angle, three sample body images reflecting three different photographing angles may be obtained.

Step 303, training a somatotype feature extraction model to be trained according to the body image set, to obtain the somatotype feature extraction model for extracting the predicted somatotype feature.

In the embodiment of the present disclosure, the initialized somatotype feature extraction model may be prepared in advance as the somatotype feature extraction model to be trained, and certainly, the already trained somatotype feature extraction model may be retrained as the somatotype feature extraction model to be trained.

In some embodiments, the parameters in the somatotype feature extraction model, a similarity calculation model and the classifier can be jointly trained. For example, when the above method uses the somatotype identification model for calculation, the somatotype identification model includes a somatotype feature extraction sub-model, a similarity calculation sub-model, and a classification sub-model, and the somatotype feature extraction sub-model is used to perform feature extraction on the body image to obtain the predicted somatotype feature of the user, the similarity calculation sub-model is used to perform similarity comparison between the standard somatotype feature corresponding to each somatotype category and the predicted somatotype feature, to obtain the similarity corresponding to each somatotype category, and the classification sub-model is used to screen out the target somatotype category of the user from various somatotype categories.

In practical applications, the body image set is firstly divided into a training set and a test set using specific ratios such as 9:1 and 8:2, and then the training set is input into the somatotype feature extraction model to be trained for model training. The loss value of the trained somatotype feature extraction model is used as the basis for verifying whether the model is trained, that is, if the loss value does not satisfy the expected training requirements, continue training, and if it satisfies the expected training requirements, end the training. For example, the quantity of iterations may also be set, and when the training reaches a preset quantity of times, end the training. For example, the test set may be used to test the somatotype feature extraction model after each training, and the accuracy of the trained model may be used to determine whether to continue training.

It is worth noting that, in the embodiment of the present disclosure, the body image set obtained by the perspective transformation is used to train the somatotype feature extraction model, which is suitable for the body image set that contains sample body images that can reflect multiple different photographing angles. Therefore, the somatotype feature extraction model can identify the image features of the same user's somatotype category at different photographing angles. Compared with the related art, which only uses sample images obtained under a single photographing angle for training, the present disclosure can effectively avoid the problem that the somatotype category of the body image cannot be accurately recognized due to the changeable photographing angle.

Figure 8:
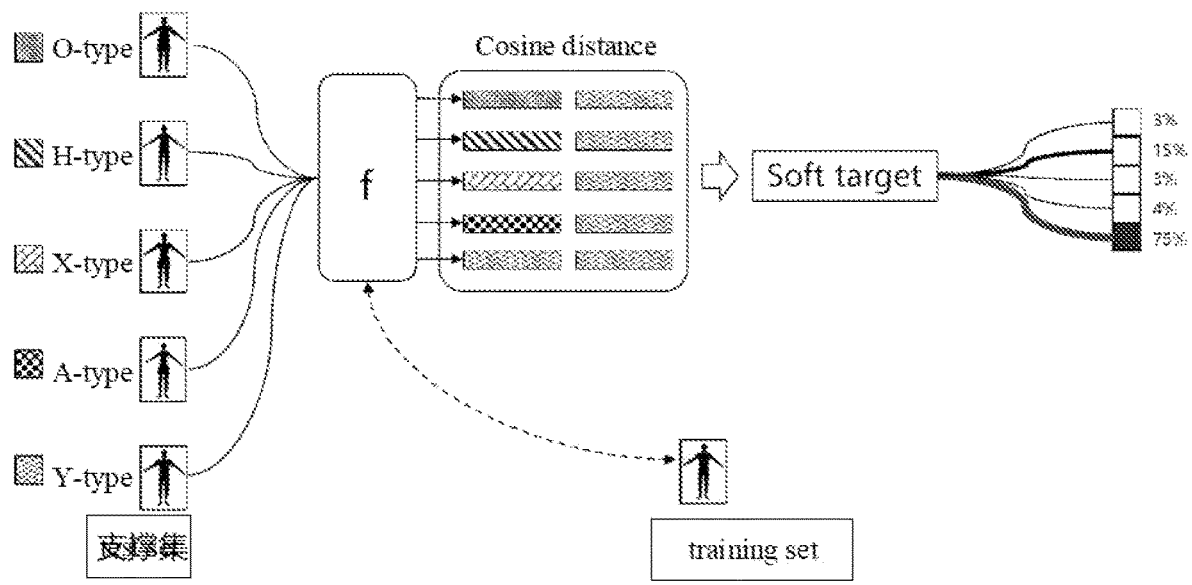
FIG. 8 schematically illustrates a second schematic diagram of a training method of a somatotype feature extraction model according to some embodiments of the present disclosure.

Exemplarily, referring to FIG. 8, the training data (the training set) and the test data (the test set) are input into the feature extraction network f, in order to prevent the gradient from disappearing, f uses resnet34 as the backbone (expense), and other types such as VGG, inception, etc., may also be used, to calculate the cosine distance between the feature extraction vectors, that is, the cosine similarity, and then obtain the results by passing through the soft target. After experiments, due to the increased depth of the resnet34 feature extraction network, the output features are not easy to degrade, which can effectively solve the problems of feature degradation and gradient disappearance caused by the increase of the network depth of the model during the model training process. Furthermore, the body image is used as the input of the feature extraction network, the output feature extraction vector is used as the predicted somatotype feature of the present disclosure, and the cosine similarity between the predicted somatotype feature and the standard somatotype feature is calculated to reflect the similarity between the predicted somatotype feature and the standard somatotype feature. Considering that using the soft target as the classifier can effectively improve the performance of the model obtained by small sample training, the present disclosure uses the soft target to integrate the obtained similarities, to obtain the probability value of the user being each somatotype category, so that the final obtained probability value can take into account various body types, and eliminate as much as possible the disadvantages of the model's inaccurate feature recognition due to fewer samples.

In the embodiment of the present disclosure, the body image set obtained by performing perspective transformation on the sample body image is used. Since the perspective transformation can make the sample body image to reflect the image features under different photographing angles, the somatotype feature extraction model obtained by training the body image set can accurately identify the somatotype category under different photographing angles, and overcome the problem of inaccurate prediction of the somatotype feature extraction model due to the variable photographing angle as much as possible, thereby improving the accuracy of somatotype identification.

Figure 9:
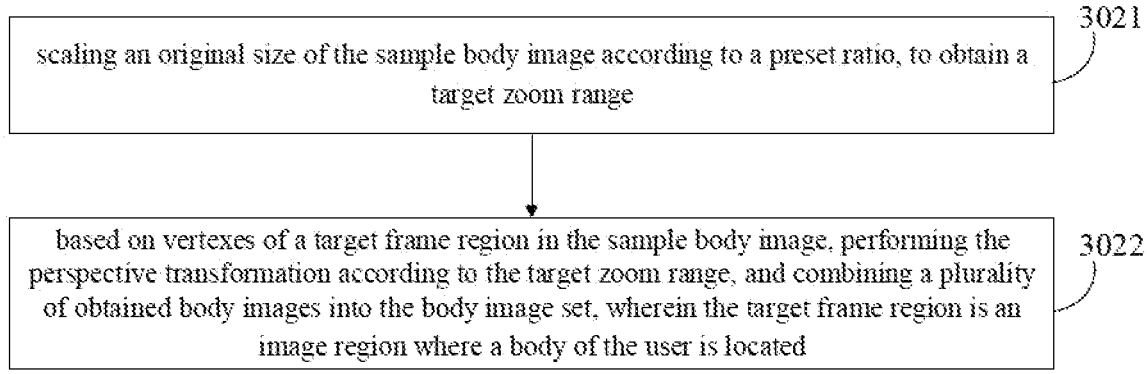
FIG. 9 schematically illustrates a second flow chart of a training method of a somatotype feature extraction model according to some embodiments of the present disclosure.

Optionally, referring to FIG. 9, the step 302 includes:

sub-step 3021, scaling an original size of the sample body image according to a preset ratio, to obtain a target zoom range.

In the embodiment of the present disclosure, the preset ratio refers to the ratio with the sample body image as the basis of reference, which may be preset according to actual needs. By scaling the original size of the sample body image according to the preset ratio, that is, the size range between the original size of the body image and the size after the original size is scaled according to the preset ratio is regarded as the target zoom range. For example, in order to ensure that the deformation of the randomly generated image is within a reasonable range, 20% of the quantity of rows and columns is selected as the preset ratio. Since the zoom ratio of the original size is 0%, the target zoom range is 0%~20% of the original size of the sample body image, a zoom ratio is randomly selected from the target zoom range to scale the sample body image to generate 1000 groups. Taking a picture with a pixel size of 380*560 as an example, the vertex coordinate of the original size of the sample body image is [(0,0), (0,380), (560,0), (380,560)], if the target zoom range is 0%~20%, the target zoom range of the abscissa is (380*0%~380*20%), that is (0~75), the target zoom range of the ordinate is (560*0%~560*20%), that is (0~111).

Figure 10:
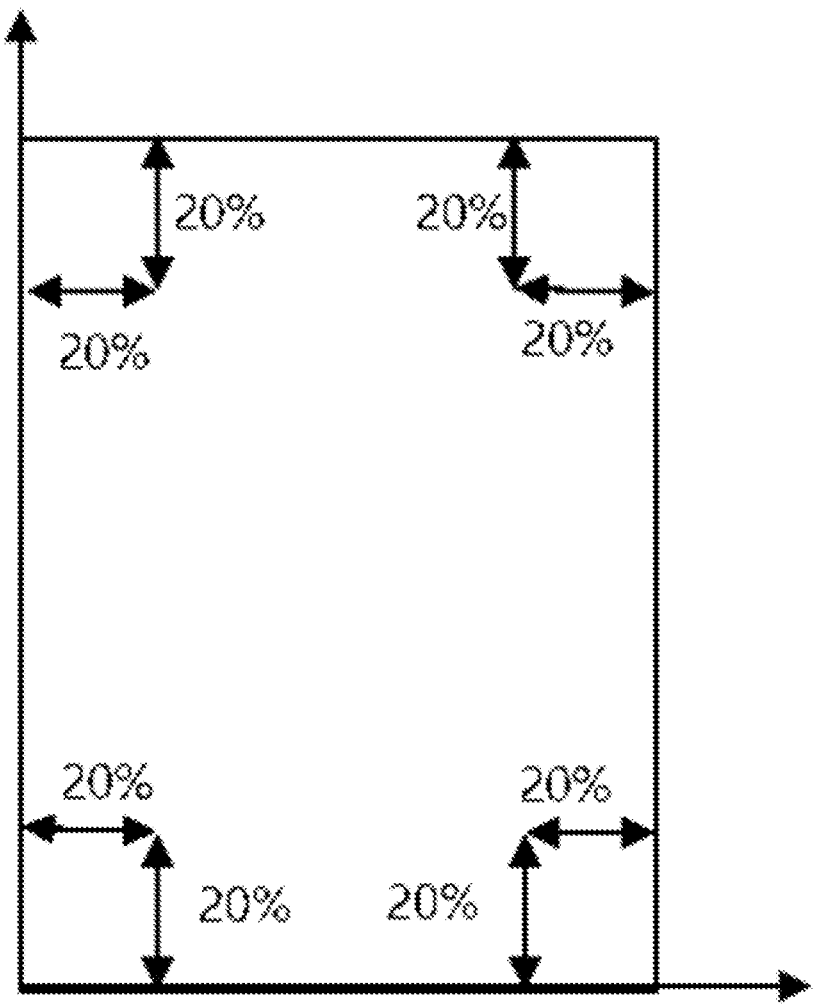
FIG. 10 schematically illustrates a third schematic diagram of a training method of a somatotype feature extraction model according to the present disclosure.

Exemplarily, referring to FIG. 10, the preset ratio may be set to 20%, so that the size range of the image extending equidistantly from the four vertices to the center of the image by 0% to 20% is used as the target zoom range.

Sub-step 3022, based on vertexes of a target frame region in the sample body image, performing the perspective transformation according to the target zoom range, and combining a plurality of obtained body images into the body image set, wherein the target frame region is an image region where a body of the user is located.

In the embodiment of the present disclosure, the target frame region is the frame image region where the user's body is located in the sample body image, the target frame region is smaller than or equal to the size of the sample body image, and its position in the sample body image may be arbitrarily set, as long as the position of the user's body in the sample body image may be specified. In some embodiments of the present disclosure, the four vertexes of the target frame region may be used as transformation parameters of the perspective transformation, to scale according to the target zoom ratio, a body image set composed of several sample body images with different photographing angles may be obtained. For example, referring to FIG. 7, the dashed frame in the body image is the target frame region, the size of the target frame region is obviously smaller than the size of the body image, and multiple body images with different photographing angles are obtained by regarding the four vertexes of the target frame region as the transformation parameters of the perspective transformation.

Wherein, the quantity of images in the body image set may be set according to the quantity of times to extract the zoom ratio from the target zoom range, and each time the value is taken, the quantity of images may be increased by one, and there is no limit to the quantity of times of value acquisition. For example, if 4 times of data are selected from the target zoom range in the example of the above sub-step 3021, such as 13, 51, 33, 42 and 75, 22, 5, 68, the new coordinates after performing the perspective transformed are [(0+13, 0+75), (0+51, 380−22), (560−33, 0+5), (380−42, 560−68)], that is [(13,75), (51,358), (527,5), (338,492)].

Figure 11:
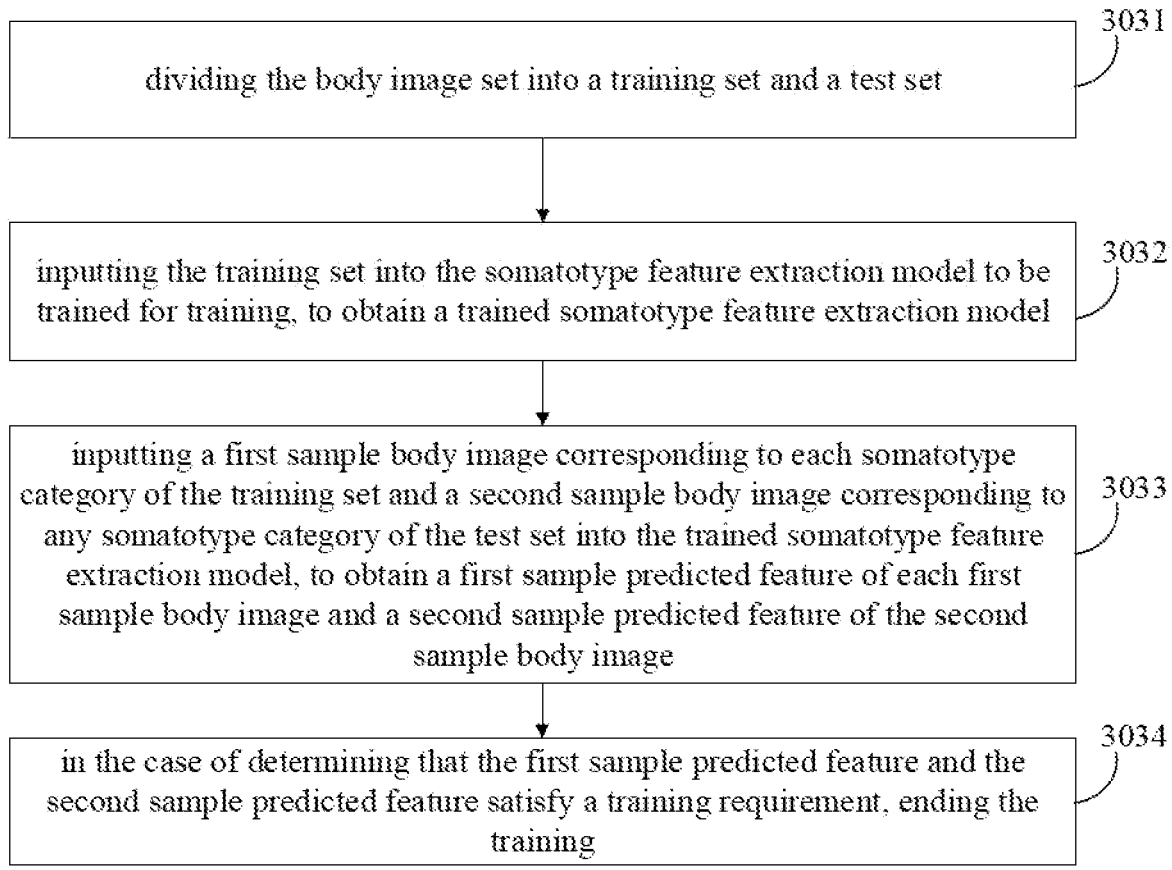
FIG. 11 schematically illustrates a third flow chart of a training method of a somatotype feature extraction model according to some embodiments of the present disclosure.

Optionally, referring to FIG. 11, the step 303 includes:

sub-step 3031, dividing the body image set into a training set and a test set.

In the embodiment of the present disclosure, for the division manner of the body image set, reference may be made to the division manner of the training set and the test set in the related art, which will not be repeated here.

Sub-step 3032, inputting the training set into the somatotype feature extraction model to be trained for training, to obtain a trained somatotype feature extraction model.

In the embodiment of the present disclosure, for the training method of the somatotype feature extraction model, reference may be made to the training method of the deep learning model in the related art, which will not be repeated here.

Sub-step 3033, inputting a first sample body image corresponding to each somatotype category of the training set and a second sample body image corresponding to any somatotype category of the test set into the trained somatotype feature extraction model, to obtain a first sample predicted feature of each first sample body image and a second sample predicted feature of the second sample body image.

In the embodiment of the present disclosure, after each training of the somatotype feature extraction model, one first sample body image is selected from the training set corresponding to each somatotype category, and then one second sample body image corresponding to any somatotype category is randomly selected from the test set, a total of n+1 sample body images are used as input, and the feature extraction network is used together to obtain n first sample predicted features and one second sample predicted feature, respectively, where n is the quantity of the somatotype categories.

Sub-step 3034, in the case of determining that the first sample predicted feature and the second sample predicted feature satisfy a training requirement, ending the training.

In the embodiment of the present disclosure, the first sample predicted feature and the second sample predicted feature may be determined according to training requirements such as similarity comparison, loss value, etc., to confirm whether the training of the somatotype feature extraction model is completed, and if the training requirements are satisfied, then confirm the training is completed, end the training, and if the training requirements are not satisfied, continue the training until the training requirements are satisfied.

Figure 12:
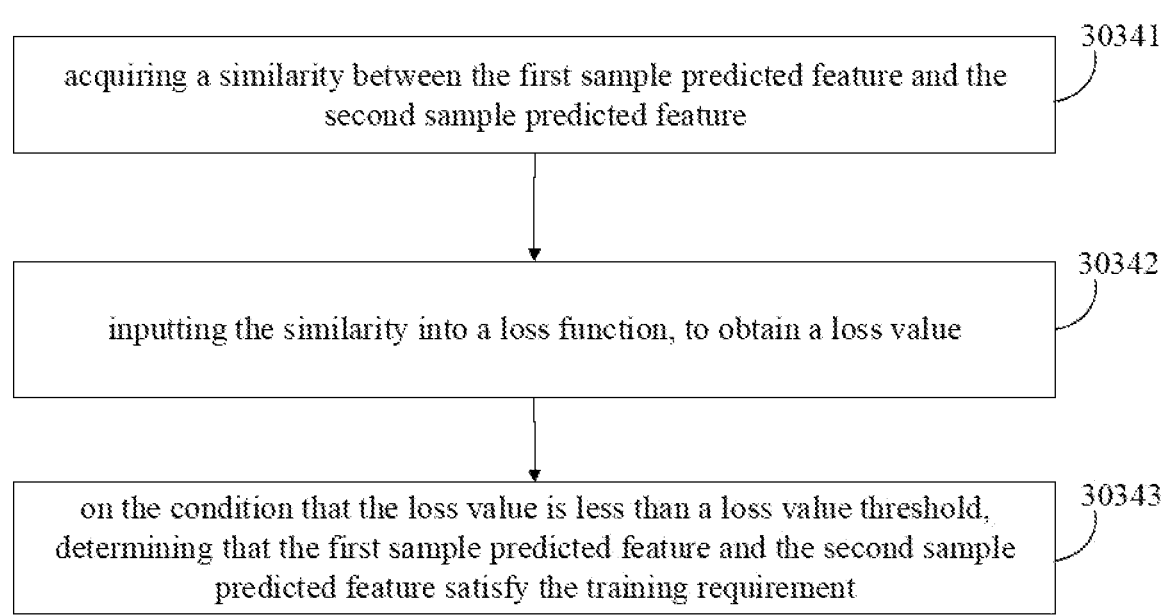
FIG. 12 schematically illustrates a fourth flow chart of a training method of a somatotype feature extraction model according to some embodiments of the present disclosure.

Optionally, referring to FIG. 12, the sub-step 3034 includes:

sub-step 30341, acquiring a similarity between the first sample predicted feature and the second sample predicted feature.

In the embodiment of the present disclosure, the calculation method of the similarity between the first sample predicted feature and the second sample predicted feature may refer to the calculation method of calculating the similarity between two feature vectors in the related art, wherein the two feature vectors are the first sample predicted feature and the second sample predicted feature, respectively, according to the embodiment of the present disclosure, and which is not be repeated here.

Sub-step 30342, inputting the similarity into a cross-entropy loss function, to obtain a loss value.

In some embodiments, the obtained value of the similarity between each first sample predicted feature and the second sample predicted feature is input into the classifier, to obtain the classification probability value of the user being each somatotype category. The classifier can be, for example, the following formula (3):

$$\hat{y} = \frac{e^{c(f(\hat{x}),f(x_i))}}{\sum_{m=1}^{k} e^{c(f(\hat{x}),f(x_m))}}. \quad (3)$$

Wherein, $f(\hat{x})$ is the second sample predicted feature, $f(x_i)$ is the first sample predicted feature for the $i^{th}$ somatotype category, $f(x_m)$ is the first sample predicted feature for the $m^{th}$ somatotype category, c represents the similarity, $0<m\leq k$, $0<i\leq k$, k is the quantity of the somatotype categories, and i, m, k are positive integer.

In some embodiments provided by the present disclosure, if the quantity of the sample body images contained in the training set is 5, the k may be set to 5, that is, k is consistent with the quantity of the sample body images in the training set. So that the obtained similarity may consider the influencing factors of the overall sample, thereby improving the accuracy of the obtained similarity.

In some embodiments, a sample is selected from the training set of each somatotype category, and a sample of a category is randomly selected from the test set (with one-shot coding as the label), a total of 6 pictures are used as input, and the feature extraction network is used together, 6 feature maps are obtained. The cosine similarity is calculated by the feature map extracted by the sixth test set and the feature maps extracted by the first five training sets, a 1*5 similarity vector is obtained and input into the cross-entropy loss function to calculate the loss. It is worth noting that one-shot refers to only one sample per category participates in training when training, which belongs to a limit state of few-shot, and few-shot refers to several samples of each category participating in training, usually the features of several samples of the same category are added bit by bit to obtain a total feature vector for similarity classification.

In the embodiment of the present disclosure, the loss value of the somatotype feature extraction model may be calculated by the following formula (4):

$$\mathrm{Loss}(\hat{y}, y) = -\sum_{j=1}^{k} y_j * \log \hat{y} \quad (4)$$

Wherein, $\hat{y}$ indicates the predicted probability value of each somatotype category, y is the standard probability value (label), k is the quantity of samples, $y_j$ is the probability value of a $j^{th}$ somatotype category, and $\mathrm{Loss}(\hat{y}, y)$ is the loss value. The calculation method of the probability value may refer to formula 2 in sub-step 30342, which will not be repeated here.

Sub-step 30343, on the condition that the loss value is less than a loss value threshold, determining that the first sample predicted feature and the second sample predicted feature satisfy the training requirement.

In the embodiment of the present disclosure, the loss value threshold is preset according to actual training requirements, and if the loss value of the trained somatotype feature extraction model is less than the loss value threshold, it means that the trained somatotype feature extraction model has achieved the expected effect, which may satisfy the training requirements, the training is stopped, and the somatotype feature extraction model can be released for use. For example, it is also possible to set a threshold for the quantity of iterative training times, when the threshold for the quantity of iterative training times is reached, it means that the trained somatotype feature extraction model has achieved the expected effect, which can satisfy the training requirements. Then the training is stopped and the somatotype feature extraction model can be released for use.

Figure 13:
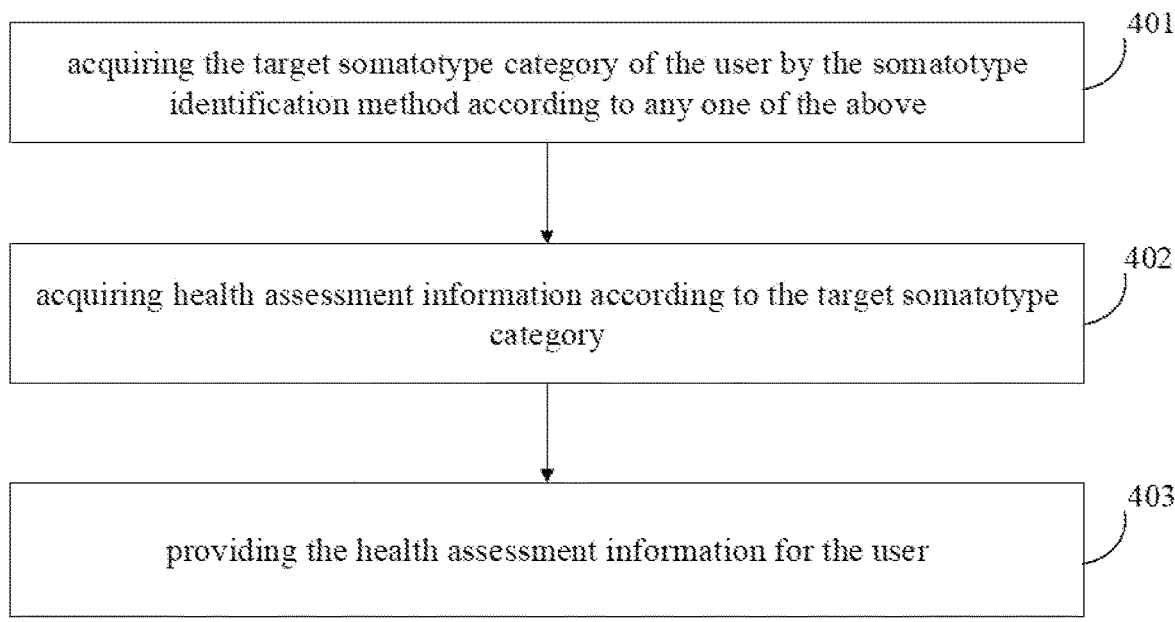
FIG. 13 schematically illustrates a first flow chart of an acquisition method of health assessment according to some embodiments of the present disclosure.

FIG. 13 schematically illustrates a flow chart of an acquisition method of health assessment according to the present disclosure, and the method includes:

step 401, acquiring the target somatotype category of the user by the somatotype identification method according to any one of the above embodiments.

For this step, reference may be made to the detailed description of any of the above-mentioned somatotype identification methods, which will not be repeated here.

Step 402, acquiring health assessment information according to the target somatotype category.

In the embodiment of the present disclosure, the health assessment information is a prediction result that users of different somatotype categories may have health risks. In some embodiments of the present disclosure, the association relationship between different somatotype categories and health assessment information may be set based on actual diagnosis and treatment experience or experimental data. For example, the health assessment information corresponding to the O-type somatotype category is: fatty liver, diabetes, hypertension, hyperlipidemia, coronary heart disease, arteriosclerosis, etc.; the health assessment information corresponding to the H-type somatotype category is: males have no obvious disease manifestations, females have digestive system disorders, endocrine disorders, menopausal syndrome, etc., in common; the health assessment information corresponding to the X-type somatotype category is: no obvious disease manifestations, but it is necessary to focus on the exercise of the waist and abdominal muscles; the health assessment information corresponding to the A-type somatotype category is: varicose veins and other problems; the health assessment information corresponding to the Y-type somatotype category is: no obvious disease manifestations. Certainly, this is only an exemplary description, and the specific acquisition method of health assessment information may also be set according to actual needs, which is not limited here.

Step 403, providing the health assessment information for the user.

In some embodiments provided by the present disclosure, the system can query the corresponding health assessment information according to the user's somatotype category output by the somatotype feature extraction model, and send it to the client-side, the client-side outputs through audio, video, audio and video and other output methods, and display it to the user, so that the user can easily understand the possible health risks of their own somatotype category, or output directly locally, as long as the user can obtain the health assessment information, which is not limited here.

In the embodiment of the present disclosure, the somatotype feature extraction model is used to identify the user's body image, to determine the user's target somatotype category according to the predicted features output by the somatotype feature extraction model. The somatotype category of the user may be accurately identified without relying on somatotype templates, which improves the accuracy of somatotype identification, and by outputting the corresponding health assessment information according to the determined somatotype category for the user to view, the user may easily know his own health assessment information.

Figure 14:
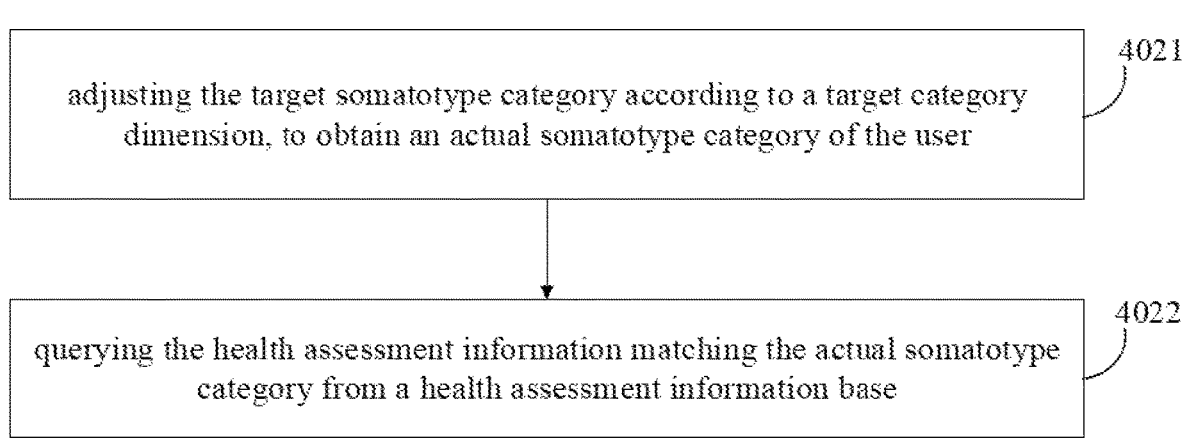
FIG. 14 schematically illustrates a second flow chart of an acquisition method of health assessment according to some embodiments of the present disclosure.

Optionally, referring to FIG. 14, the step 402 may include:

sub-step 4021, adjusting the target somatotype category according to a target category dimension, to obtain an actual somatotype category of the user.

The above target category dimension may be obtained through the terminal device receiving the corresponding dimension information input by the user, and may also be obtained through the user-corresponding dimension information database. Wherein, the user-corresponding dimension information database may be constructed through the user information obtained by conducting a questionnaire survey on the user, or further constructed through the user information obtained by analyzing the users historical behavior data.

In the embodiment of the present disclosure, the target category dimension refers to the refined classification dimension of the somatotype category, and may specifically refer to the gender dimension. For example, when the gender includes male and female, the A somatotype category, B somatotype category, and C somatotype category may be refined as: male A somatotype category, male B somatotype category, male C somatotype category, female A somatotype category, female B somatotype category, female C somatotype category; or the age dimension, such as childhood, prime age, old age, the A somatotype category and B somatotype category may be further refined as: childhood A somatotype category, childhood B somatotype category, adult A somatotype category, adult B somatotype category, aged A somatotype category, aged B somatotype category. Certainly, the sub-somatotype category may also be further divided according to specific category dimensions. The division method is similar to the above method, and which is not be repeated here. The specific division method of the somatotype category may be set according to actual needs, and which is not limited here.

Sub-step 4022, querying the health assessment information matching the actual somatotype category from a health assessment information base.

In the embodiment of the present disclosure, the health assessment information corresponding to various actual somatotype categories may be collected in advance, to establish an association relationship between the actual somatotype categories and the health assessment information, so as to generate the health assessment information base. Therefore, in the actual use, the required health assessment information may be efficiently queried in the health assessment information base according to the actual somatotype category.

Optionally, the step 402 may include: querying disease prediction information matching the actual somatotype category from the health assessment information base as the health assessment information of the user.

In the embodiment of the present disclosure, the disease prediction information is the disease prediction risk that may exist in different actual somatotype categories, for example, an obese somatotype may have a disease risk such as fatty liver and hyperglycemia. Health advice information is a life improvement plan that may be taken for different actual somatotype categories. For example, for the obese somatotype, users may be suggested to increase exercise, eat more fruits and vegetables, and eat less high-calorie food, while for a thin somatotype, users may be advised to increase exercise, and eat more high-protein and high-calorie foods, etc., the specific disease prediction information and health advice information may be set for different actual somatotype categories according to actual needs, which are not limited here. Certainly, the disease prediction information may be obtained firstly, and then use the disease prediction information to match and obtain health improvement suggestions as the user's health assessment information, which can be set according to actual needs, and which is not limited here.

Figure 15:
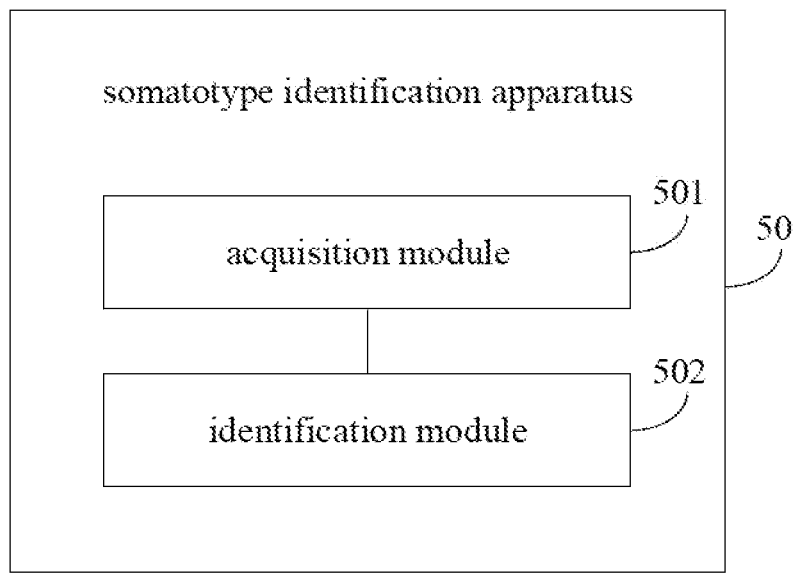
FIG. 15 schematically illustrates a structural schematic diagram of a somatotype identification apparatus according to some embodiments of the present disclosure.

FIG. 15 schematically illustrates a structural schematic diagram of a somatotype identification apparatus 50 according to the present disclosure, and the apparatus includes:

an acquisition module 501, configured to acquire a body image of a user;

an identification module 502, configured to perform a feature extraction on the body image, to obtain a predicted somatotype feature of the user; and screen a target somatotype category of the user from various somatotype categories according to the predicted somatotype feature.

Optionally, the identification module 502 is further configured to:

perform a similarity comparison between a standard somatotype feature corresponding to each somatotype category and the predicted somatotype feature, to obtain a similarity corresponding to each somatotype category;

calculate the similarity corresponding to each somatotype category by a classifier, to obtain a probability value of the user being each somatotype category; and regard a somatotype category corresponding to a probability value that satisfies a probability value screening rule as the target somatotype category of the user.

Optionally, the identification module 502 is further configured to:

acquire a sort of probability values of various somatotype categories; and according to a somatotype category of which the sort of probability values is a target probability value sort, acquire the target somatotype category of the user.

Optionally, at least two target probability value sorts exist; the identification module is further configured to:

acquire at least two target probability values which are probability values being the target probability value sorts, from the probability values corresponding to the various somatotype categories;

on the condition that a difference value between the at least two target probability values is greater than a probability threshold, regard a somatotype category corresponding to the target probability value with a maximum value as the target somatotype category of the user; and on the condition that the difference value between the at least two target probability values is less than or equal to the probability threshold, regard somatotype categories corresponding to the at least two target probability values, respectively, as the target somatotype categories of the user.

Optionally, the target probability value sorts include: a probability value sort being the first and a probability value sort being the second;

the identification module 502 is further configured to:

acquire a first probability value with the sort of probability values being the first and a second probability value with the sort of probability values being the second, from the probability values corresponding to the various somatotype categories, wherein the sort of probability values is sorted in descending order.

Optionally, the identification module 502 is further configured to:

input the similarity corresponding to each somatotype category into the following classifier formula, to obtain the probability value of the user being each somatotype category:

$$\text{soft target} = \frac{\exp(c(f(\hat{x}), f(x_i))/T)}{\sum_m \exp(c(f(\hat{x}), f(x_m))/T)}$$

wherein, the soft target is the probability value of a type category, $f(\hat{x})$ is the predicted somatotype feature, $f(x_i)$ is the standard somatotype feature for an $i^{th}$ somatotype category, $f(x_m)$ is the standard somatotype feature for a $m^{th}$ somatotype category, T is a constant parameter, $c(f(\hat{x}), f(x_i))$ is the similarity between the predicted somatotype feature and the $i^{th}$ standard somatotype feature, $c(f(\hat{x}), f(x_m))$ is the similarity between the predicted somatotype feature and the $m^{th}$ standard somatotype feature, $0<m\leq k$, $0<i\leq k$, k is a quantity of the somatotype categories, and i, m, k are positive integer, and the similarity includes at least one of the followings: a cosine similarity, a sine similarity, a Pearson coefficient, and a Jaccard coefficient.

Optionally, the identification module 502 is further configured to:

input the body image into a somatotype feature extraction model, to obtain the predicted somatotype feature of the user, wherein the somatotype feature extraction model is obtained by the following steps:

acquire a sample body image labeled with the somatotype category;

perform a perspective transformation on the sample body image, to obtain a body image set; and train a somatotype feature extraction model to be trained according to the body image set, to obtain the somatotype feature extraction model for extracting the predicted somatotype feature.

Optionally, the identification module 502 is further configured to:

based on vertexes of a target frame region in the sample body image, perform the perspective transformation according to a target zoom range, and combine a plurality of obtained body images into the body image set, wherein the target frame region is an image region where a body of the user is located.

Optionally, the identification module 502 is further configured to:

scale an original size of the sample body image according to a preset ratio, to obtain the target zoom range.

Optionally, the identification module 502 is further configured to:

divide the body image set into a training set and a test set;

input the training set into the somatotype feature extraction model to be trained for training, to obtain a trained somatotype feature extraction model;

input a first sample body image corresponding to various somatotype categories of the training set and a second sample body image corresponding to any somatotype category of the test set into the trained somatotype feature extraction model, to obtain a first sample predicted feature of each first sample body image and a second sample predicted feature of the second sample body image; and in the case of determining that the first sample predicted feature and the second sample predicted feature satisfy a training requirement, end the training.

Optionally, the identification module 502 is further configured to:

acquire a sample similarity between the first sample predicted feature and the second sample predicted feature;

input the sample similarity into a loss function, to obtain a loss value;

on the condition that the loss value satisfies a model training requirement, determine that the first sample predicted feature and the second sample predicted feature satisfy the training requirement.

In the embodiment of the present disclosure, the somatotype feature extraction model is used to identify the user's body image, so as to determine the user's target somatotype category according to the predicted features output by the somatotype feature extraction model. The somatotype category of the user may be accurately identified without relying on the somatotype templates, thereby improving the accuracy of the somatotype identification.

Figure 16:
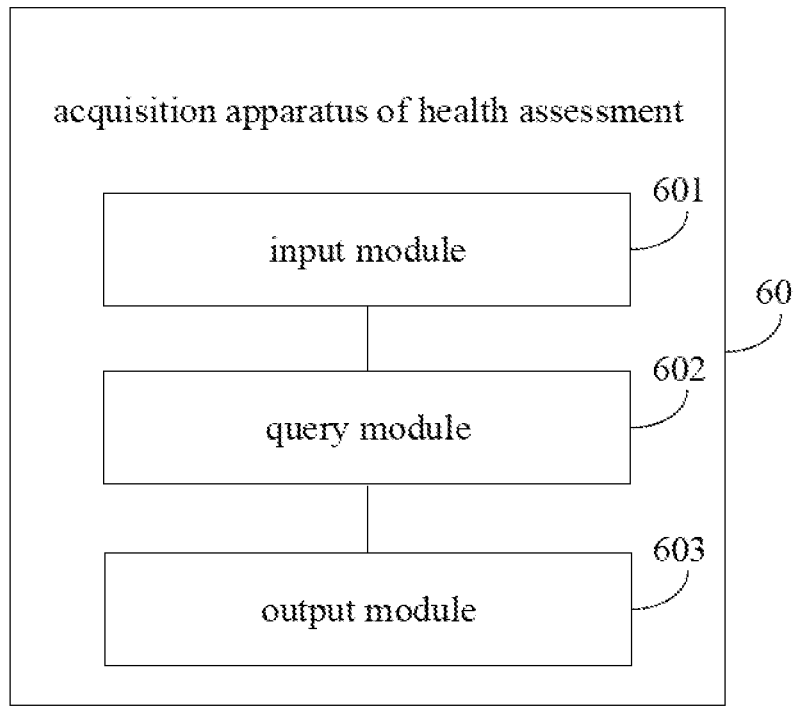
FIG. 16 schematically illustrates a structural schematic diagram of an acquisition apparatus of health assessment according to some embodiments of the present disclosure.

FIG. 16 schematically illustrates a structural schematic diagram of an acquisition apparatus of health assessment 60 according to the present disclosure, and the apparatus includes:

an input module 601, configured to acquire the target somatotype category of the user by the somatotype identification method according to any one of the above embodiments;

a query module 602, configured to acquire health assessment information according to the target somatotype category; and an output module 603, configured to provide the health assessment information for the user.

Optionally, the query module 602 is further configured to:

adjust the target somatotype category according to a target category dimension, to obtain an actual somatotype category of the user; and query the health assessment information matching the actual somatotype category from a health assessment information base.

Optionally, the query module 602 is further configured to:

query disease prediction information matching the actual somatotype category from the health assessment information base as the health assessment information of the user.

In the embodiment of the present disclosure, the somatotype feature extraction model is used to identify the user's body image, to determine the user's target somatotype category according to the predicted features output by the somatotype feature extraction model. The somatotype category of the user may be accurately identified without relying on the somatotype templates, thereby improving the accuracy of the somatotype identification. And by outputting the corresponding health assessment information according to the determined somatotype category for the user to view, the user may easily know his own health assessment information.

The device embodiments described above is only schematic, the units illustrated as separated parts may be or may not be separated physically, and the parts shown in unit may be or may not be a physical unit. That is, the parts may be located at one place or distributed in multiple network units. A skilled person in the art may select part or all modules therein to realize the objective of achieving the technical solution of the embodiment. Those of ordinary skill in the art can understand and implement it without creative effort.

Each of devices according to the embodiments of the disclosure can be implemented by hardware, or implemented by software modules operating on one or more processors, or implemented by the combination thereof. A person skilled in the art should understand that, in practice, a microprocessor or a digital signal processor (DSP) may be used to realize some or all of the functions of some or all of the modules in the device according to the embodiments of the disclosure. The disclosure may further be implemented as device program (for example, computer program and computer program product) for executing some or all of the methods as described herein. Such program for implementing the disclosure may be stored in the computer readable medium, or have a form of one or more signals. Such a signal may be downloaded from the internet websites, or be provided in carrier, or be provided in other manners.

Figure 17:
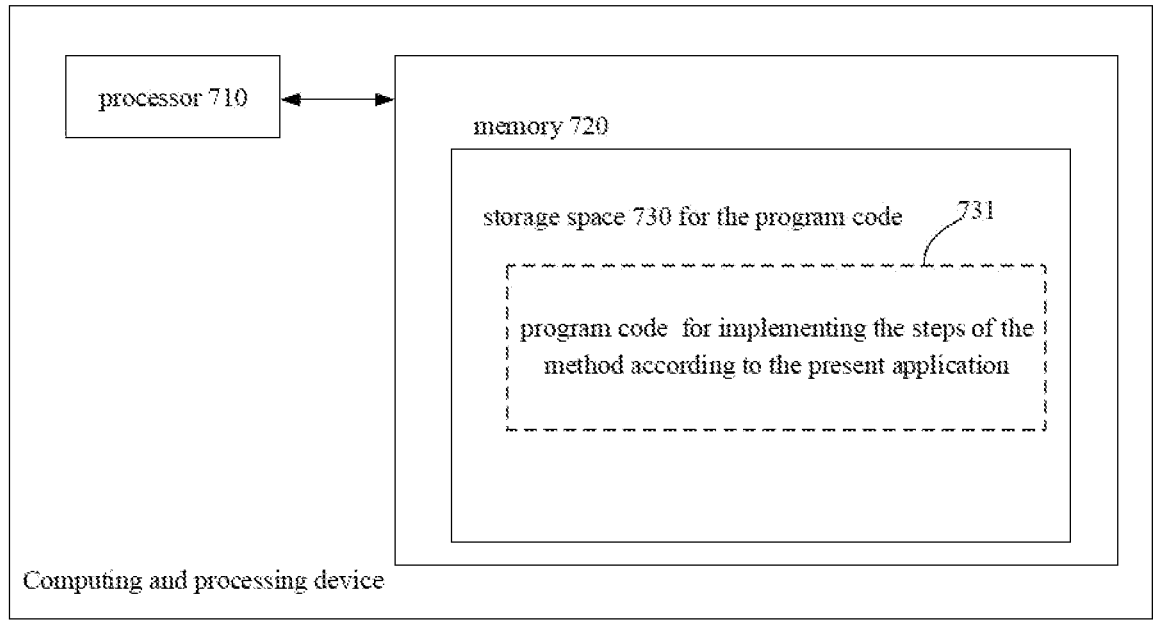
FIG. 17 schematically shows a block diagram of a computing and processing device for implementing the method according to some embodiments of the present disclosure.
Figure 18:
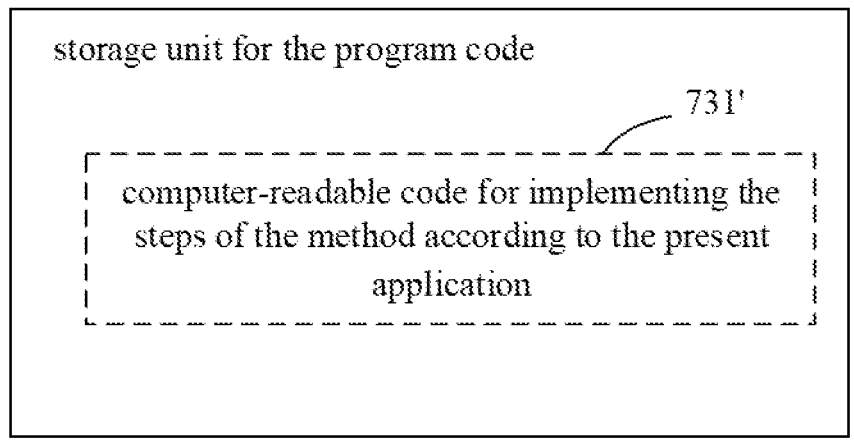
FIG. 18 schematically shows a storage unit for maintaining or carrying a program code for implementing the method according to some embodiments of the present disclosure.

For example, FIG. 17 illustrates a block diagram of a computing and processing device for executing the method according the disclosure. Traditionally, the computing and processing device includes a processor 710 and a computer program product or a computer readable medium in form of a memory 720. The memory 720 could be electronic memories such as flash memory, EEPROM (Electrically Erasable Programmable Read-Only Memory), EPROM, hard disk or ROM. The memory 720 has a memory space 730 for executing program codes 731 of any steps in the above methods. For example, the memory space 730 for program codes may include respective program codes 731 for implementing the respective steps in the method as mentioned above. These program codes may be read from and/or be written into one or more computer program products. These computer program products include program code carriers such as hard disk, compact disk (CD), memory card or floppy disk. These computer program products are usually the portable or stable memory cells as shown in reference FIG. 18. The memory cells may be provided with memory sections, memory spaces, etc., similar to the memory 720 of the server as shown in FIG. 17. The program codes may be compressed for example in an appropriate form. Usually, the memory cell includes computer readable codes 731' which can be read for example by processors 710. When these codes are operated on the server, the server may execute respective steps in the method as described above.

It should be understood that, although the various steps in the flow chart of the accompanying drawings are sequentially shown in the order indicated by the arrows, these steps are not necessarily executed in sequence in the order indicated by the arrows. Unless explicitly stated herein, the execution of these steps is not strictly limited to the order and may be performed in other orders. Moreover, at least a part of the steps in the flow chart of the accompanying drawings may include multiple sub-steps or multiple stages, and these sub-steps or stages are not necessarily executed at the same moment, but may be executed at different timings, and the execution sequence does not have to be performed sequentially, but may be performed alternately or alternately with other steps or at least a portion of sub-steps or stages of other steps.

The "an embodiment", "embodiments" or "one or more embodiments" mentioned in the disclosure means that the specific features, structures, or performances described in combination with the embodiment(s) would be included in at least one embodiment of the disclosure. Moreover, it should be noted that, the wording "in an embodiment" herein may not necessarily refer to the same embodiment.

Many details are discussed in the specification provided herein. However, it should be understood that the embodiments of the disclosure can be implemented without these specific details. In some examples, the well-known methods, structures, and technologies are not shown in detail so as to avoid an unclear understanding of the description.

In the claims, any reference signs between parentheses should not be construed as limiting the claims. The word "comprise" does not exclude elements or steps that are not listed in the claims. The word "a" or "an" preceding an element does not exclude the existing of a plurality of such elements. The present application may be implemented by means of hardware comprising several different elements and by means of a properly programmed computer. In unit claims that list several devices, some of those devices may be embodied by the same item of hardware. The words first, second, third and so on do not denote any order. Those words may be interpreted as names.

Finally, it should be noted that the above embodiments are merely intended to explain the technical solutions of the present application, and not to limit them. Although the present application is explained in detail by referring to the above embodiments, a person skilled in the art should understand that he can still modify the technical solutions set forth by the above embodiments, or make equivalent substitutions to part of the technical features of them. However, those modifications or substitutions do not make the essence of the corresponding technical solutions depart from the spirit and scope of the technical solutions of the embodiments of the present application.

The invention claimed is:

1. A somatotype identification method, wherein the method comprises:
   acquiring a body image of a user;
   performing a feature extraction on the body image, to obtain a predicted somatotype feature of the user; and
   screening a target somatotype category of the user from various somatotype categories according to the predicted somatotype feature;
   wherein performing the feature extraction on the body image, to obtain a predicted somatotype feature of the user, comprises:
   inputting the body image into a somatotype feature extraction model, to obtain the predicted somatotype feature of the user, wherein the somatotype feature extraction model is obtained by the following steps:
   acquiring a sample body image labeled with the somatotype category;
   performing a perspective transformation on the sample body image, to obtain a body image set; and
   training a somatotype feature extraction model to be trained according to the body image set, to obtain the somatotype feature extraction model for extracting the predicted somatotype feature;
   wherein performing a perspective transformation on the sample body image, to obtain a body image set, comprises:
   based on vertexes of a target frame region in the sample body image, performing the perspective transformation according to a target zoom range, and combining a plurality of obtained body images into the body image set, wherein the target frame region is an image region where a body of the user is located.

2. The method according to claim 1, wherein screening the target somatotype category of the user from the various somatotype categories according to the predicted somatotype feature comprises:
   performing a similarity comparison between a standard somatotype feature corresponding to each somatotype category and the predicted somatotype feature, to obtain a similarity corresponding to each somatotype category;
   calculating the similarity corresponding to each somatotype category by a classifier, to obtain a probability value of the user being each somatotype category; and
   regarding a somatotype category corresponding to a probability value that satisfies a probability value screening rule as the target somatotype category of the user.

3. The method according to claim 2, wherein regarding the somatotype category corresponding to the probability value that satisfies the probability value screening rule as the target somatotype category of the user comprises:
   acquiring a sort of probability values of various somatotype categories; and
   according to a somatotype category of which the sort of probability values is a target probability value sort, acquiring the target somatotype category of the user.

4. The method according to claim 3, wherein at least two target probability value sorts exist;
   the according to the somatotype category of which the sort of probability values is the target probability value sort, acquiring the target somatotype category of the user, comprises:
   acquiring at least two target probability values which are probability values being the target probability value sorts, from the probability values corresponding to the various somatotype categories;
   on the condition that a difference value between the at least two target probability values is greater than a probability threshold, regarding a somatotype category corresponding to the target probability value with a maximum value as the target somatotype category of the user; and
   on the condition that the difference value between the at least two target probability values is less than or equal to the probability threshold, regarding somatotype categories corresponding to the at least two target probability values, respectively, as the target somatotype categories of the user.

5. The method according to claim 4, wherein the target probability value sorts comprise: a probability value sort being the first and a probability value sort being the second;
   the acquiring at least two target probability values which are probability values being the target probability value sorts, from the probability values corresponding to the various somatotype categories, comprises:
   acquiring a first probability value with the sort of probability values being the first and a second probability value with the sort of probability values being the second, from the probability values corresponding to the various somatotype categories, wherein the sort of probability values is sorted in descending order.

6. The method according to claim 2, wherein calculating the similarity corresponding to each somatotype category by the classifier, to obtain the probability value of the user being each somatotype category, comprises:
   inputting the similarity corresponding to each somatotype category into the following classifier formula, to obtain the probability value of the user being each somatotype category:

$$\text{soft target} = \frac{\exp(c(f(\hat{x}), f(x_i))/T)}{\sum_m \exp(c(f(\hat{x}), f(x_m))/T)}$$

wherein, the soft target is the probability value of a type category, $f(\hat{x})$ is the predicted somatotype feature, $f(x_i)$ is the standard somatotype feature for an $i^{th}$ somatotype category, $f(x_m)$ is the standard somatotype feature for a $m^{th}$ somatotype category, T is a constant parameter, $c(f(\hat{x}), f(x_i))$ is the similarity between the predicted somatotype feature and the $i^{th}$ standard somatotype feature, $c(f(\hat{x}), f(x_m))$ is the similarity between the predicted somatotype feature and the $m^{th}$ standard somatotype feature, $0<m\leq k$, $0<i\leq k$, k is a quantity of the somatotype categories, and i, m, k are positive integer, and the similarity comprises at least one of the followings: a cosine similarity, a sine similarity, a Pearson coefficient, and a Jaccard coefficient.

7. The method according to claim 1, wherein before the step of based on the vertexes of the target frame region in the sample body image, performing the perspective transformation according to the target zoom range, and combining the plurality of obtained body images into the body image set, the method further comprises:
   scaling an original size of the sample body image according to a preset ratio, to obtain the target zoom range.

8. The method according to claim 1, wherein training the somatotype feature extraction model to be trained according to the body image set, to obtain the somatotype feature extraction model for extracting the predicted somatotype feature, comprises:

dividing the body image set into a training set and a test set;

inputting the training set into the somatotype feature extraction model to be trained for training, to obtain a trained somatotype feature extraction model;

inputting a first sample body image corresponding to each somatotype category of the training set and a second sample body image corresponding to any somatotype category of the test set into the trained somatotype feature extraction model, to obtain a first sample predicted feature of each first sample body image and a second sample predicted feature of the second sample body image; and in the case of determining that the first sample predicted feature and the second sample predicted feature satisfy a training requirement, ending the training.

9. The method according to claim 8, wherein determining that the first sample predicted features and the second sample predicted feature satisfy the training requirement comprises:

acquiring a sample similarity between the first sample predicted feature and the second sample predicted feature;

inputting the sample similarity into a loss function, to obtain a loss value; and on the condition that the loss value satisfies a model training requirement, determining that the first sample predicted feature and the second sample predicted feature satisfy the training requirement.

10. An acquisition method of health assessment, wherein the method comprises:

acquiring the target somatotype category of the user by the somatotype identification method according to claim 1;

acquiring health assessment information according to the target somatotype category; and providing the health assessment information for the user.

11. The method according to claim 10, wherein acquiring health assessment information according to the target somatotype category comprises:

adjusting the target somatotype category according to a target category dimension, to obtain an actual somatotype category of the user; and querying the health assessment information matching the actual somatotype category from a health assessment information base.

12. The method according to claim 11, wherein querying the health assessment information matching the actual somatotype category from a health assessment information base comprises:

querying disease prediction information matching the actual somatotype category from the health assessment information base as the health assessment information of the user.

13. A first computing and processing device, comprising:
a first memory storing a first computer-readable code; and
one or more first processors, wherein when the first computer-readable code is executed by the one or more first processors, the first computing and processing device implements the somatotype identification method according to claim 1.

14. A first non-transitory computer-readable medium, wherein the first non-transitory computer-readable medium stores a first computer-readable code, when the first computer-readable code is executed on a first computing and processing device, the first computing and processing device implements the somatotype identification method according to claim 1.

15. A second computing and processing device, comprising:

a second memory storing a second computer-readable code; and one or more second processors, wherein when the second computer-readable code is executed by the one or more second processors, the second computing and processing device implements the acquisition method of health assessment according to claim 10.

16. A second non-transitory computer-readable medium, wherein the second non-transitory computer-readable medium stores second computer-readable code, when the second computer-readable code is executed on a second computing and processing device, the second computing and processing device implements the acquisition method of health assessment according to claim 10.

* * * * *